United States Patent
Noda et al.

(10) Patent No.: US 8,273,943 B2
(45) Date of Patent: Sep. 25, 2012

(54) COMPOSITE SHEET AND ABSORBENT ARTICLE USING THE COMPOSITE SHEET

(75) Inventors: Yuki Noda, Kagawa (JP); Kenichiro Kuroda, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 526 days.

(21) Appl. No.: 12/516,381

(22) PCT Filed: Dec. 11, 2007

(86) PCT No.: PCT/JP2007/073870
§ 371 (c)(1),
(2), (4) Date: May 27, 2009

(87) PCT Pub. No.: WO2008/072631
PCT Pub. Date: Jun. 19, 2008

(65) Prior Publication Data
US 2010/0069867 A1 Mar. 18, 2010

(30) Foreign Application Priority Data

Dec. 12, 2006 (JP) .................................. 2006-334243

(51) Int. Cl.
*A61F 13/15* (2006.01)
(52) U.S. Cl. ........ 604/382; 604/383; 604/380; 604/378; 604/385.101
(58) Field of Classification Search .................. 604/383, 604/382, 380, 378, 385.101
See application file for complete search history.

(56) References Cited

U.S. PATENT DOCUMENTS

| 6,528,698 | B2 | 3/2003 | Mizutani et al. |
| 2004/0229008 | A1 | 11/2004 | Hoying |
| 2005/0148970 | A1 | 7/2005 | Kudo et al. |

FOREIGN PATENT DOCUMENTS

| EP | 1591089 | 11/2005 |
| JP | 02-193663 A | 7/1990 |
| JP | 03-097458 A | 4/1991 |
| JP | 2002-096878 A | 4/2002 |
| JP | 3759609 B2 | 1/2006 |
| JP | 2006-511381 A | 4/2006 |
| JP | 2008-125918 A | 6/2008 |
| JP | 2008-264077 A | 11/2008 |
| WO | 95/31166 A1 | 11/1995 |
| WO | 9619173 | 6/1996 |
| WO | 2004/058497 A1 | 7/2004 |

OTHER PUBLICATIONS

International Search Report of Application No. PCT/JP2007/073870 mailed Mar. 25, 2008.
Office Action issued to Chinese Application No. 200780045514.7, mailed Dec. 19, 2011.
Supplementary European Search Report issued to EP Application No. 07850432.1, mailed Oct. 10, 2011.

*Primary Examiner* — Jacqueline F. Stephens
(74) *Attorney, Agent, or Firm* — Lowe, Hauptman, Ham & Berner, LLP

(57) ABSTRACT

It is intended to provide an absorbent article provided with a composite sheet which comprises a film sheet and a fiber mass and is excellent in the ability to draw in a liquid and the ability to prevent the backward flow. Namely, an absorbent article provided with a composite sheet comprising a film sheet having multiple pores formed therein and a fiber mass laminated on one side of the film sheet, wherein the fiber mass has a projected section in which a part of the fiber mass projects through the multiple pores toward the other side of the film sheet.

17 Claims, 16 Drawing Sheets

WIDTH DIRECTION

LONGITUDINAL DIRECTION

LINE DIRECTION

WIDTH DIRECTION

THICKNESS DIRECTION

LINE DIRECTION/CIRCUMFERENTIAL DIRECTION

CIRCUMFERENTIAL DIRECTION

COMPOSITE SHEET AND ABSORBENT ARTICLE USING THE COMPOSITE SHEET

RELATED APPLICATIONS

The present application is based on International Application Number PCT/JP2007/073870, filed Dec. 11, 2007, and claims priority from Japanese Application Number 2006-334243, filed Dec. 12, 2006, the disclosures of which are hereby incorporated by reference herein in their entirety.

TECHNICAL FIELD

The present invention relates to a composite sheet in which a film sheet and a fiber aggregate are disposed to be layered.

BACKGROUND ART

Conventionally, improvements have been made for a shape and the like of a top sheet and a second sheet for an absorbent article such as a sanitary napkin, in order to appropriately transfer a discharged matter such as menstrual blood to an absorbent core. An example of such a sheet includes: a sheet having improved liquid drawing abilities (spot property) in a predetermined spot (position) by a plurality of fine openings, and a sheet having improved liquid drawing abilities by capillary action realized by adjusting fiber density. However, has been difficult to suppress rewet, in other words, backset of a discharged matter such as menstrual blood once absorbed by an absorbent body, in a case where a large amount of discharged matter such as menstrual blood was discharged.

On the other hand, a sanitary napkin has been proposed including a liquid permeable top sheet, a liquid impermeable back sheet bonded to the top sheet, an absorbent core disposed between the top sheet and the back sheet, and a masking member made of a liquid permeable perforated film disposed between the top sheet and the absorbent core (see Japanese Patent No. 3759609, hereinafter referred to as Patent Document 1). The masking member is characterized by being disposed along a periphery of the sanitary napkin, covering a periphery of the absorbent core, and composing an opening portion positioned in a center.

DISCLOSURE OF THE INVENTION

Problems to be Solved by the Invention

However, with the sanitary napkin disclosed in Patent Document 1, since masking with a perforated film is provided below the top sheet, although rewet (backset of liquid) can be suppressed, it may be difficult for liquid such as menstrual blood that has pooled on the top sheet to transfer to the absorbent core.

An objective of the present invention is to provide an absorbent article provided with a composite sheet having a superior liquid drawing ability and a superior rewet suppressing ability, including a film sheet and a fiber aggregate.

Means for Solving the Problems

The present inventors have found that an absorbent article provided with a composite sheet obtained by laminating a film sheet and a fiber aggregate can suppress backset of liquid (rewet) while transferring menstrual blood and the like, which is discharged, to an absorbent core, thus leading to the completion of the present invention.

According to a first aspect of the present invention, a composite sheet includes: a film sheet on which a plurality of openings and/or a plurality of slits formed; and a fiber aggregate that is disposed to be layered on one side of the film sheet, in which the composite sheet is formed such that a portion of the fiber aggregate forms a plurality of projecting regions that project to another side of the film sheet through the plurality of openings and/or the plurality of slits; a portion of the film sheet disposed between a predetermined projecting region and a projecting region disposed adjacent thereto in the plurality of projecting regions forms a U-shaped groove by continuously deforming to a U-shape projecting toward the fiber aggregate; and at least a portion of a peripheral region of each of the plurality of openings and/or the plurality of slits deforms to stand toward a projecting side of the projecting regions so as to cover at least a portion of a base portion of each of the projecting regions.

According to a second aspect of the present invention, in the composite sheet as described in the first aspect, the U-shaped groove is formed to extend in a straight line or in a curved line in a predetermined direction.

According to a third aspect of the present invention, in the composite sheet as described in the first or the second aspect, a communicating hole is formed on an apex or on a side face of the plurality of projecting regions.

According to a fourth aspect of the present invention, in the composite sheet as described in any one of the first to the third aspects, a second fiber aggregate including cellulosic fiber is further disposed to be layered on an opposite side of the film sheet to a side on which the first fiber aggregate is disposed.

In a fifth aspect of the present invention, an absorbent article includes: a top sheet that is at least partially liquid permeable, including the composite sheet as described in any one of the first to the fourth aspects in at least a portion thereof; a back sheet that is liquid impermeable; and an absorbent core which is liquid retentive, disposed between the top sheet and the back sheet, in which the composite sheet is disposed such that the plurality of projecting regions face the absorbent core.

In a sixth aspect of the present invention, an absorbent article of an elongated shape includes: a top sheet that is at least partially liquid permeable; a back sheet that is liquid impermeable; an absorbent core which is liquid retentive, disposed between the top sheet and the back sheet; and a second sheet that is at least partially liquid permeable and disposed between the top sheet and the absorbent core, including the composite sheet as described in any one of the first to fourth aspects in at least a portion thereof, in which the composite sheet is disposed such that the plurality of projecting regions face the absorbent core.

In a seventh aspect of the present invention, a method for manufacturing a composite sheet includes: a layered arranging step of forming a layered sheet by disposing substantially sheet-shaped fiber aggregate to be layered on one side of a predetermined film sheet; and a projecting region forming step of forming a plurality of projecting regions that project toward another side of the film sheet by pushing through the film sheet from a surface of an opposite side of the fiber aggregate to a side of the film sheet, to dislocate portions on the fiber aggregate by way of a predetermined projecting region forming means.

According to an eighth aspect of the present invention, in the method for manufacturing a composite sheet as described in the seventh aspect, the film sheet is a low-elasticity film sheet.

According to a ninth aspect of the present invention, in the method for manufacturing a composite sheet as described in the seventh or the eighth aspect, in the projecting region forming step, the projecting region forming means includes a first member having a flat surface or a curved surface with a plurality of openings formed thereon and a second member having a flat surface or a curved surface with a plurality of projections formed thereon corresponding to the plurality of openings, disposed such that the flat surface or the curved surface thereof faces the flat surface or the curved surface of the first member with the plurality of openings formed thereon; and in a state where the layered sheet is disposed such that a side to the film sheet faces the first member and a side to the fiber aggregate faces the second member, the layered sheet is tucked between the first member and the second member such that at least a portion of the plurality of projections formed on the second member engages at least a portion of the plurality of openings formed on the first member, so as to form a plurality of projecting regions projecting toward another side, by pushing through the film sheet to dislocate portions on the fiber aggregate by way of at least a portion of the plurality of projections.

According to a tenth aspect of the present invention, in the method for manufacturing a composite sheet as described in the ninth aspect, a draw ratio by the projections is higher than an elasticity of the film sheet in an extension direction by the projections.

Effects of the Invention

The present invention can provide an absorbent article provided with a composite sheet having superior liquid drawing ability (spot property) in a predetermined spot (position) and superior ability to suppress backset of a discharged matter such as menstrual blood, once absorbed by an absorbent core (rewet suppressing ability), and includes a film sheet and a fiber aggregate.

PREFERRED MODE FOR CARRYING OUT THE INVENTION

Preferred embodiments for implementing the present invention are described hereinafter with reference to the drawings.

Figure 1:
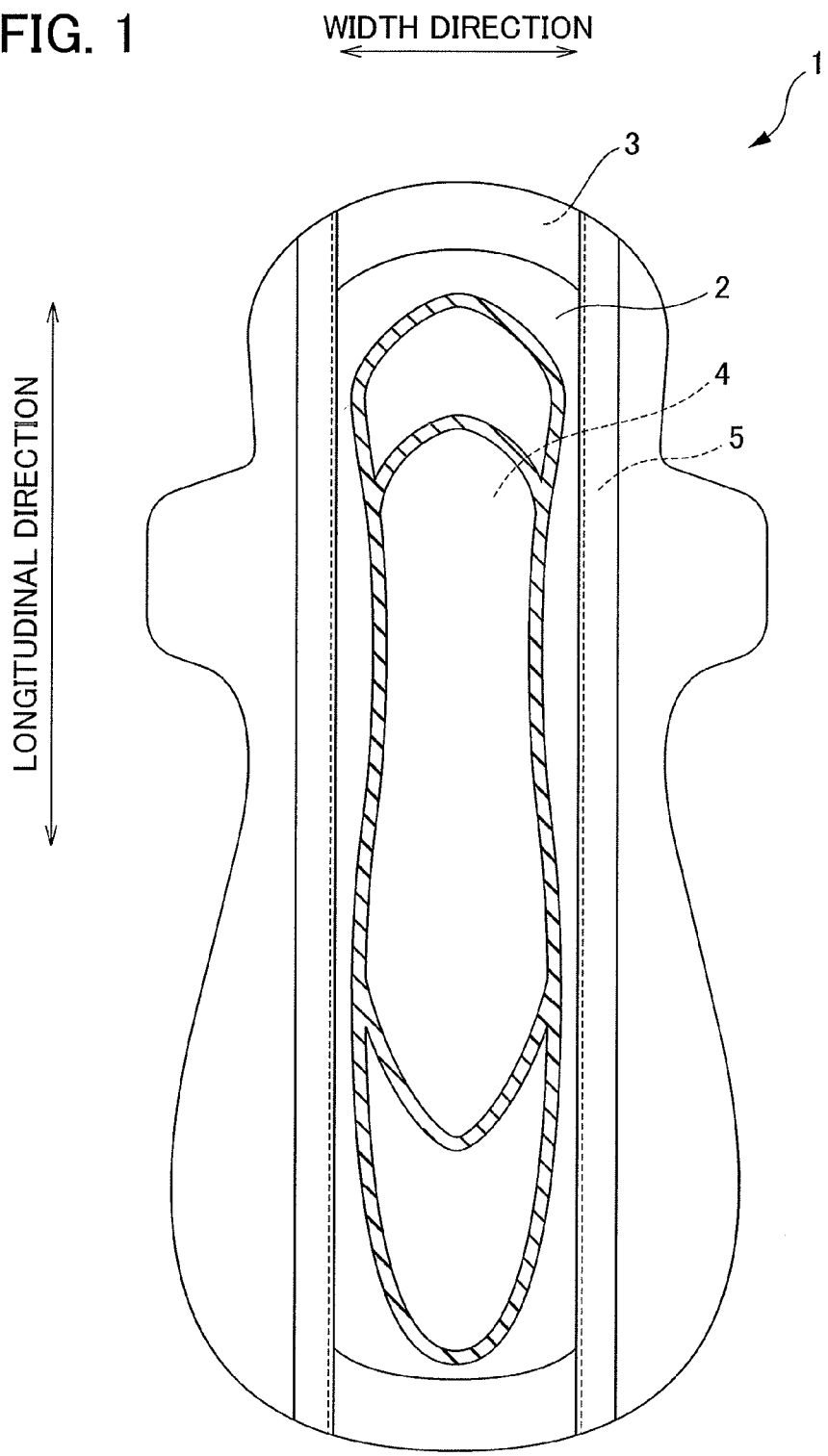
FIG. 1 is a plan view of an absorbent article according to an embodiment of the present invention.
Figure 2:
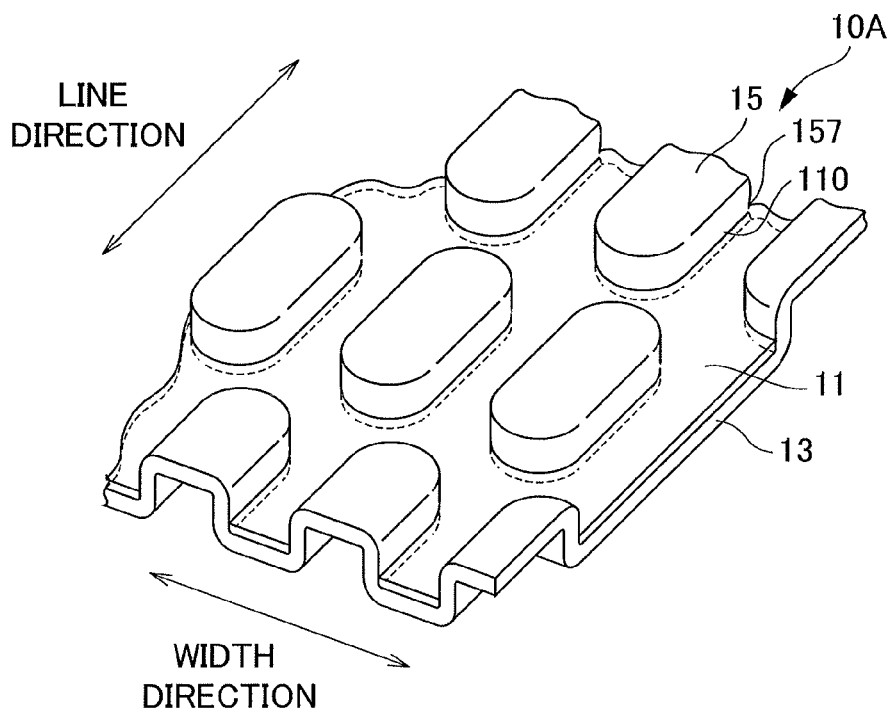
FIG. 2 is a perspective view of a composite sheet according to a first embodiment.
Figure 3:
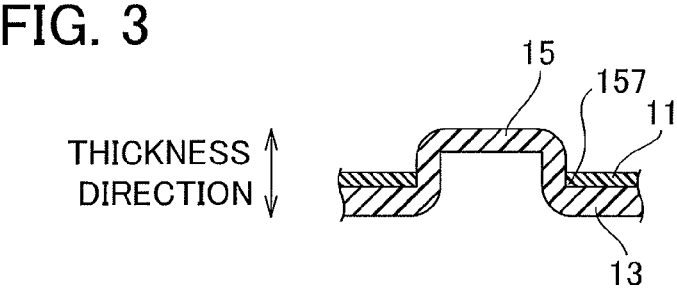
FIG. 3 is a cross-sectional view of the composite sheet according to the first embodiment.
Figure 4:
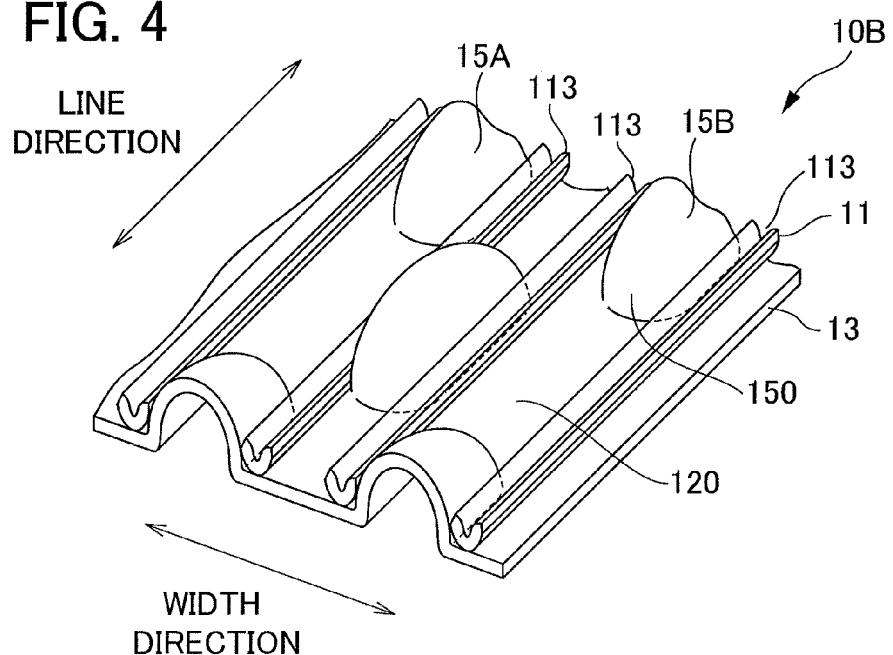
FIG. 4 is a perspective view of the composite sheet according to a second embodiment.
Figure 5:
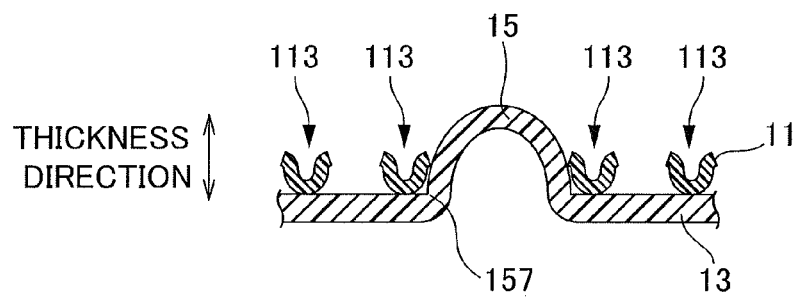
FIG. 5 is a cross-sectional view of the composite sheet according to the second embodiment.
Figure 6:
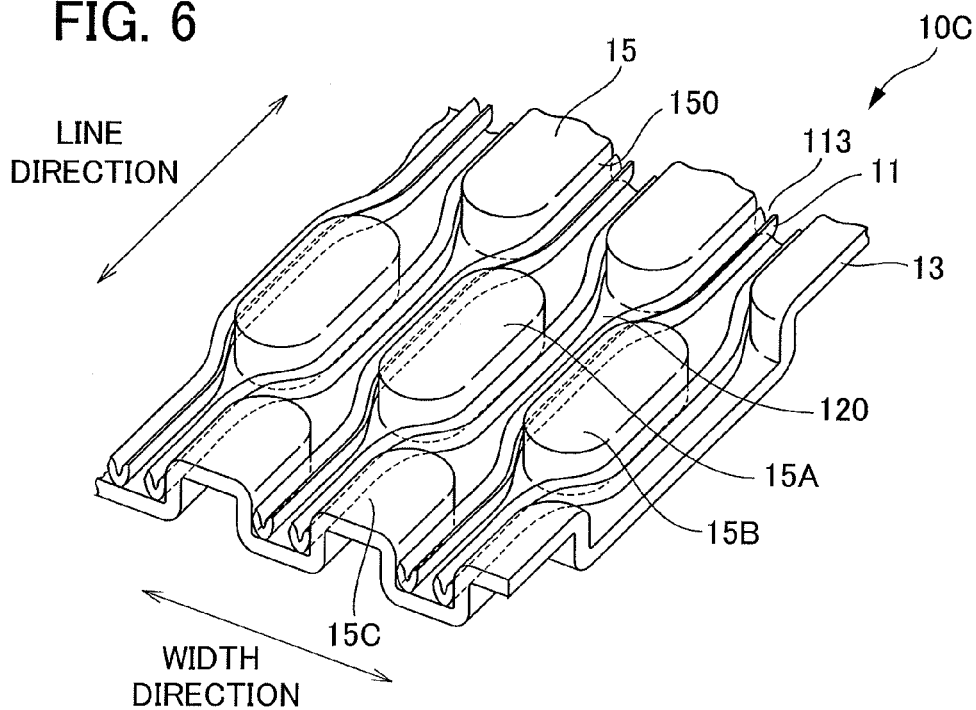
FIG. 6 is a perspective view of a composite sheet according to a third embodiment.
Figure 7:
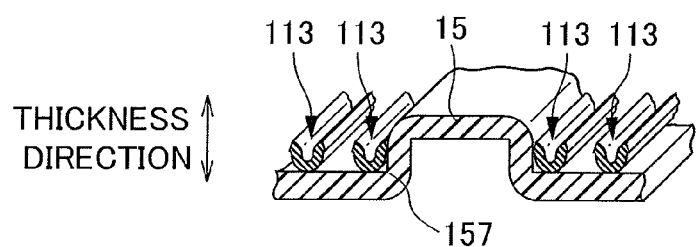
FIG. 7 is a cross-sectional view of the composite sheet according to the third embodiment.
Figure 8:
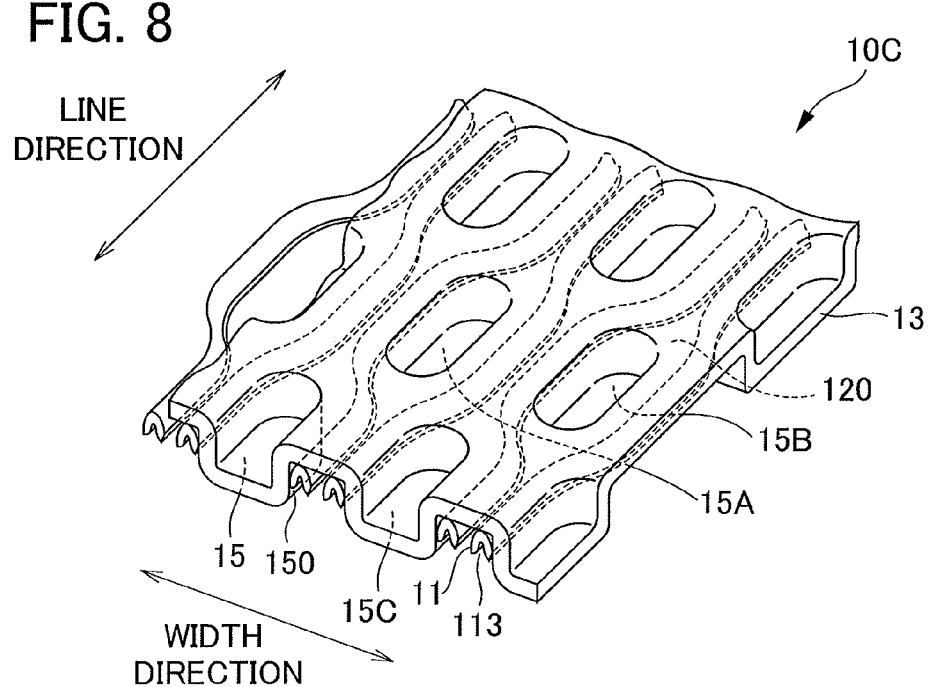
FIG. 8 is a perspective view of the composite sheet according to the third embodiment.
Figure 9:
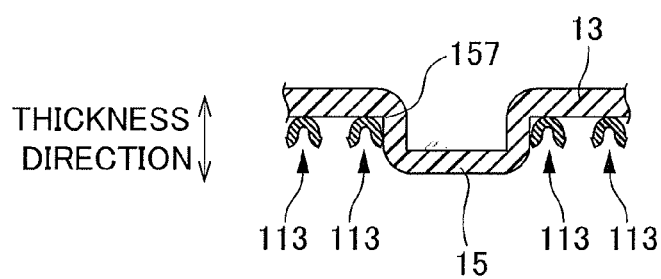
FIG. 9 is a cross-sectional view of a composite sheet according to a fourth embodiment.
Figure 10:
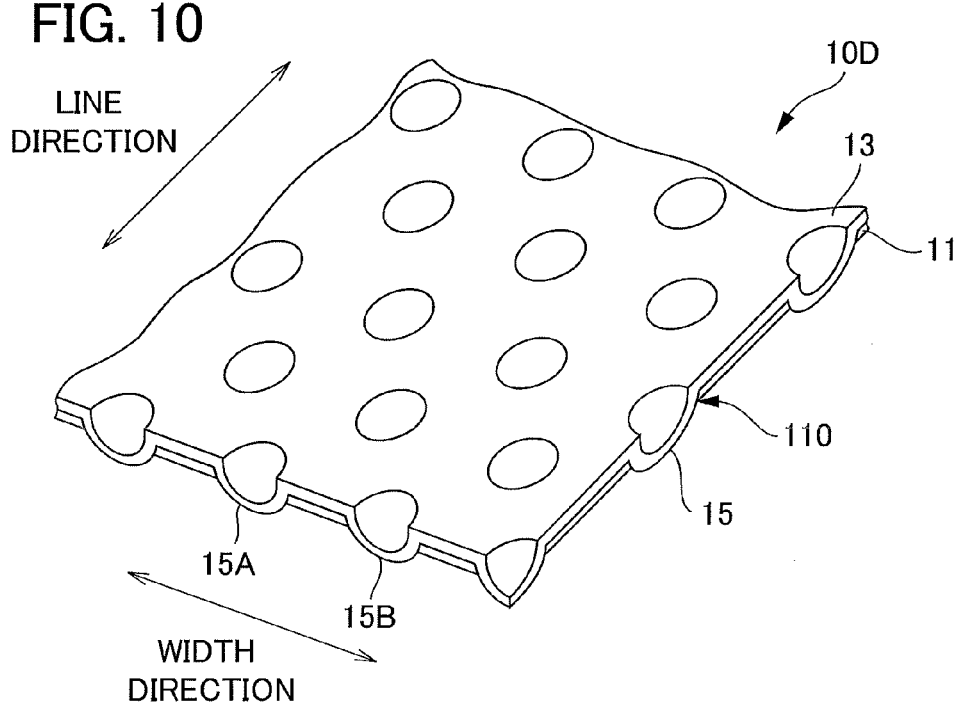
FIG. 10 is a perspective view of the composite sheet according to the fourth embodiment.
Figure 11:
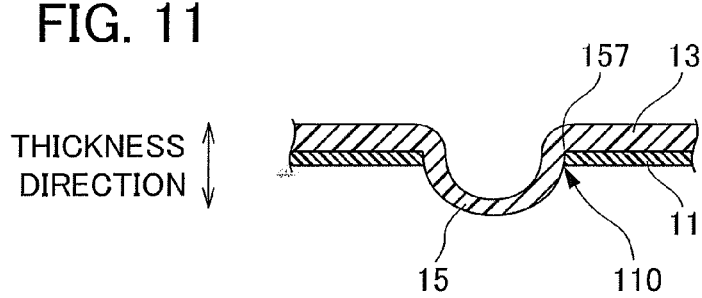
FIG. 11 is a cross-sectional view of the composite sheet according to the fourth embodiment.
Figure 12:
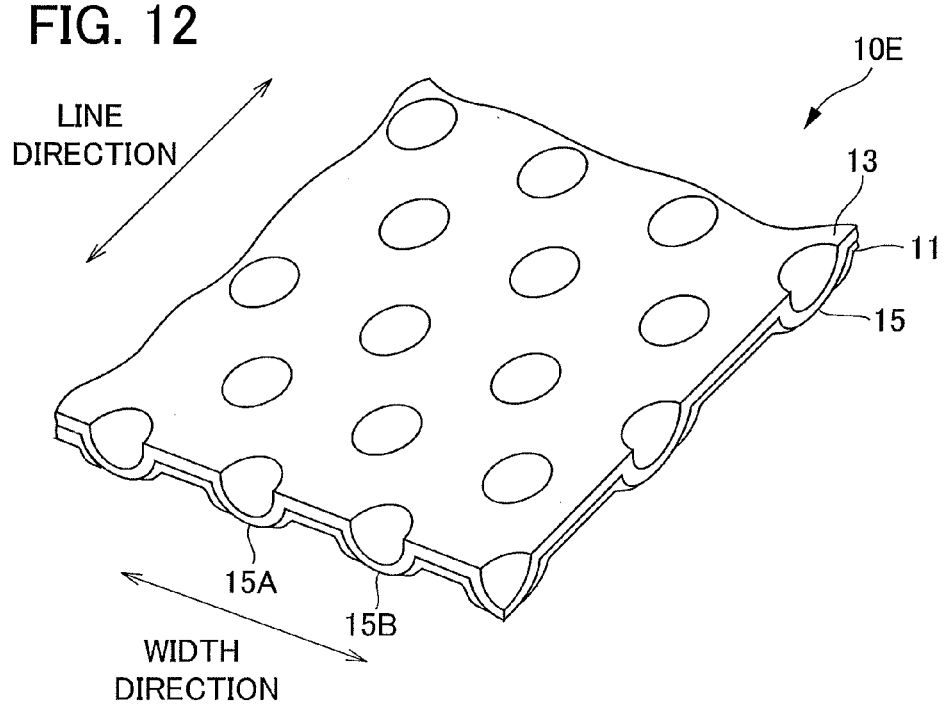
FIG. 12 is a perspective view showing a composite sheet according to a fifth embodiment.
Figure 13:
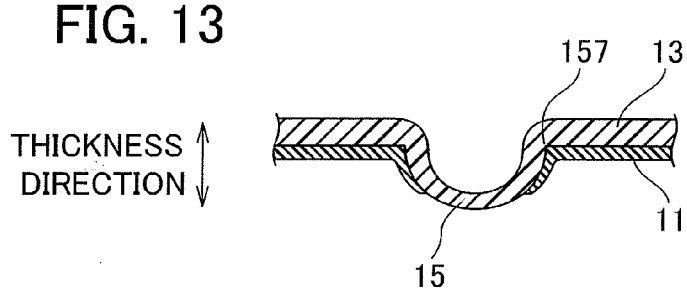
FIG. 13 is a cross-sectional view of the composite sheet according to the fifth embodiment.
Figure 14:
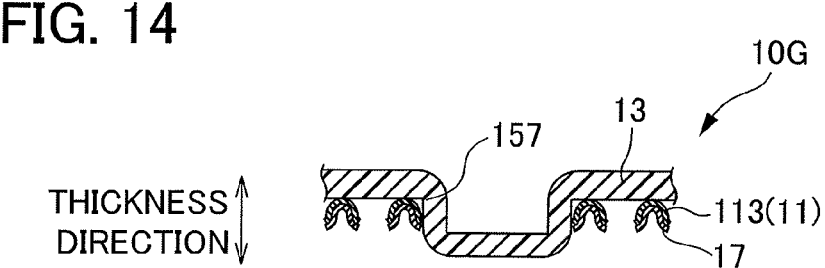
FIG. 14 is a cross-sectional view of a composite sheet according to a sixth embodiment.
Figure 15:
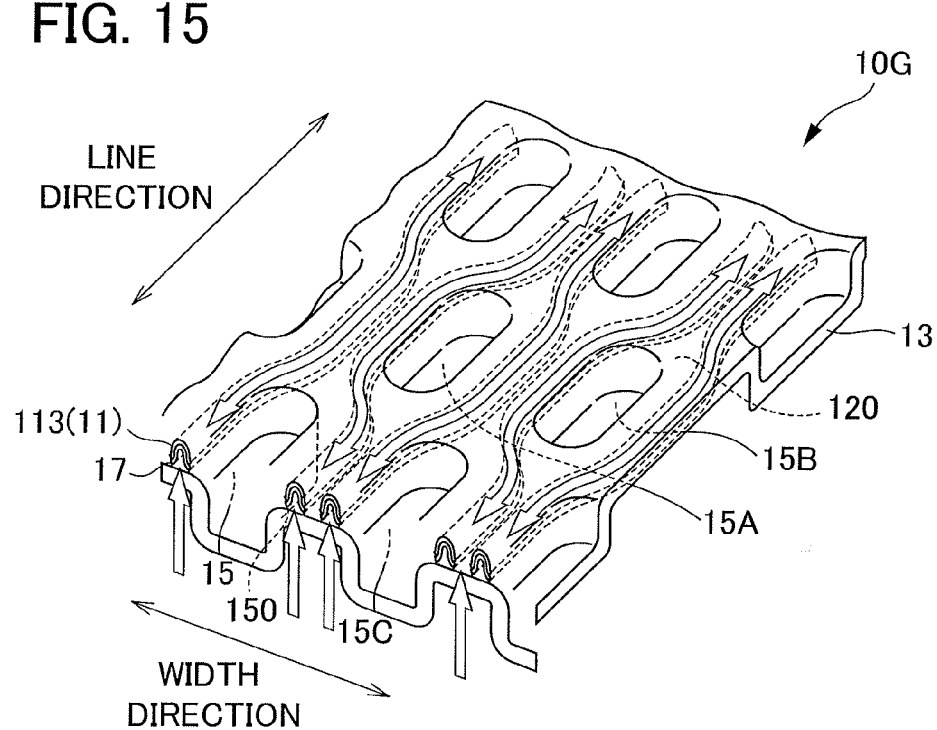
FIG. 15 is a perspective view of the composite sheet according to the sixth embodiment.
Figure 16A:
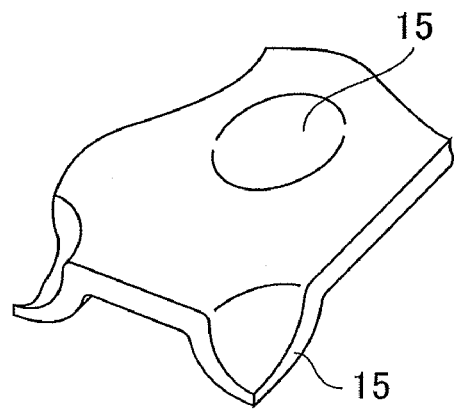
FIG. 16A is a diagram illustrating various projecting regions.
Figure 17:
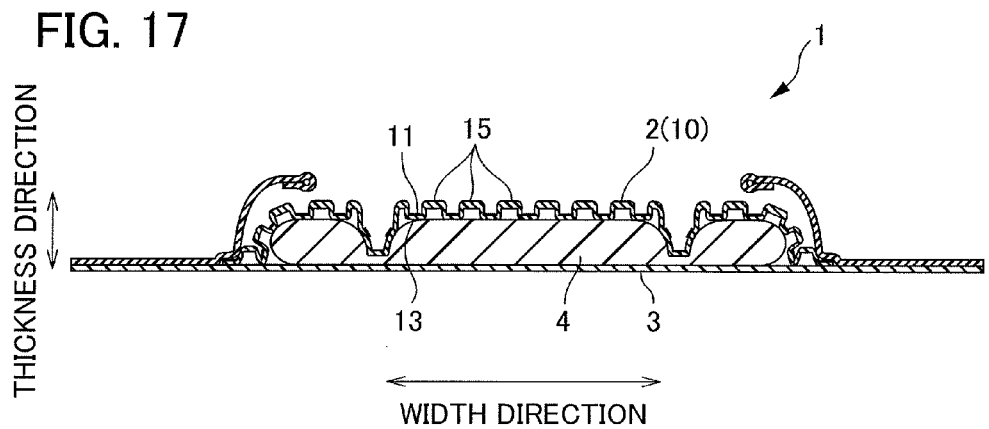
FIG. 17 is a cross-sectional view of an absorbent article using the composite sheet as a top sheet.
Figure 18:
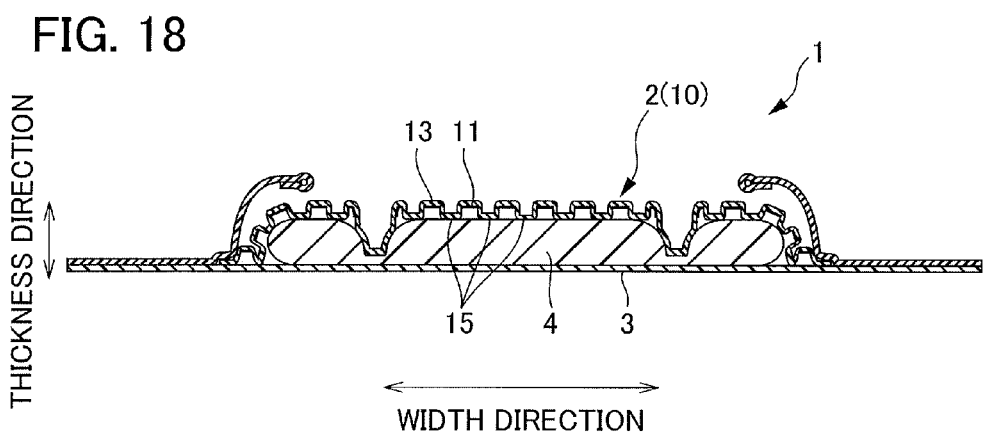
FIG. 18 is a cross-sectional view of an absorbent article using the composite sheet as a top sheet.
Figure 19:
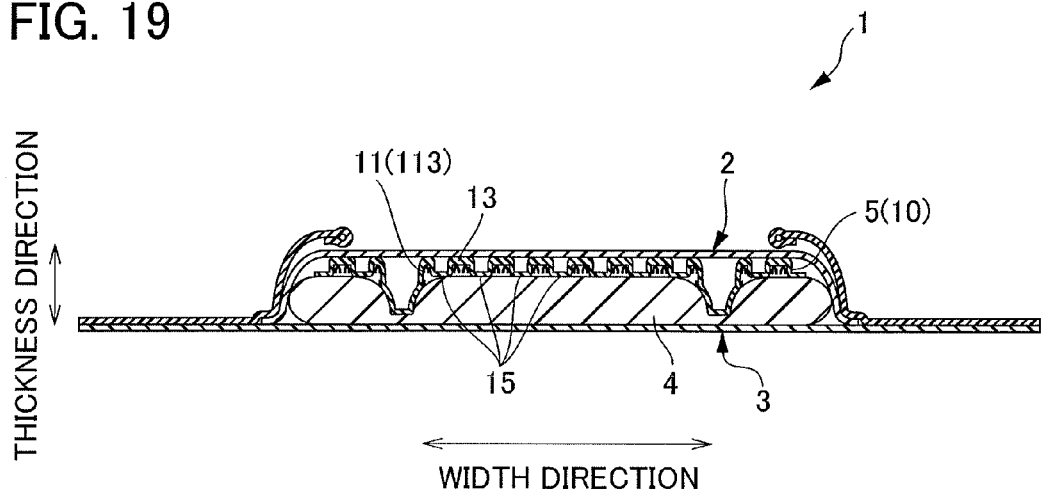
FIG. 19 is a cross-sectional view of an absorbent article using the composite sheet as a second sheet.
Figure 20:
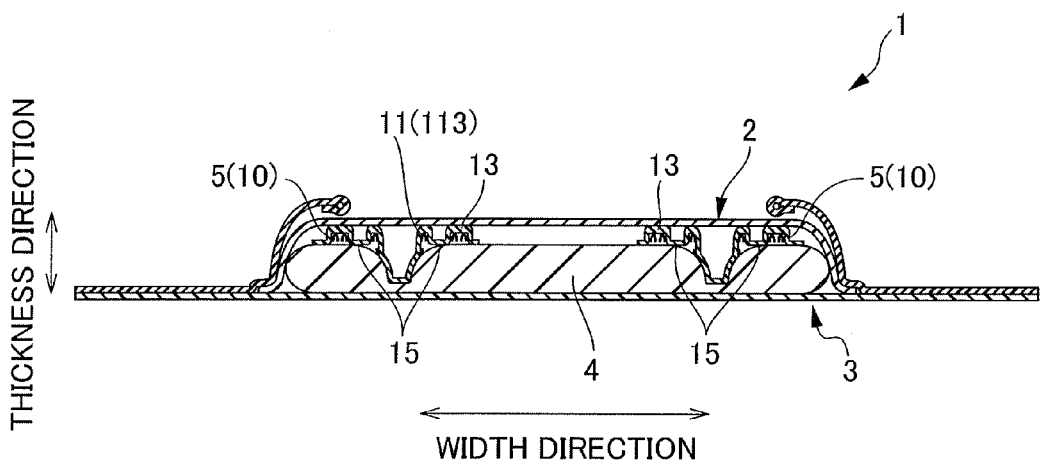
FIG. 20 is a cross-sectional view of an absorbent article using the composite sheet as a second sheet.
Figure 21:
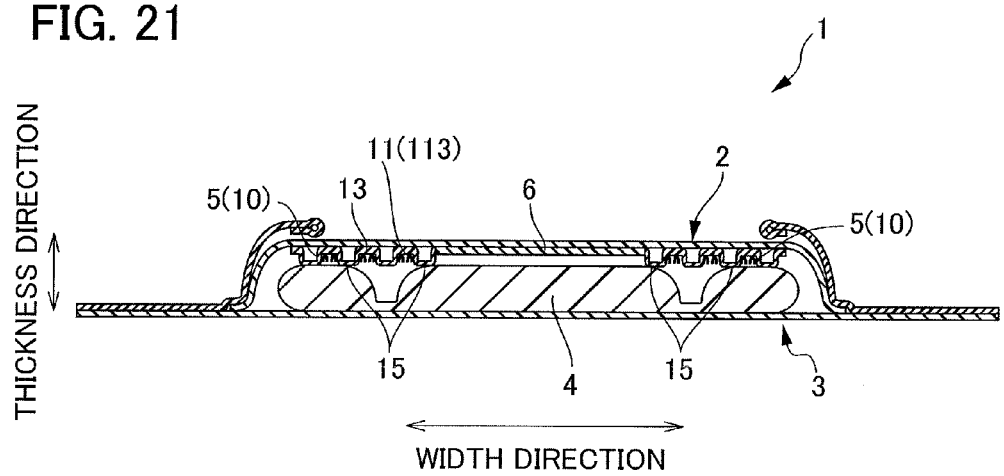
FIG. 21 is a cross-sectional view of an absorbent article using the composite sheet as a second sheet.
Figure 22:
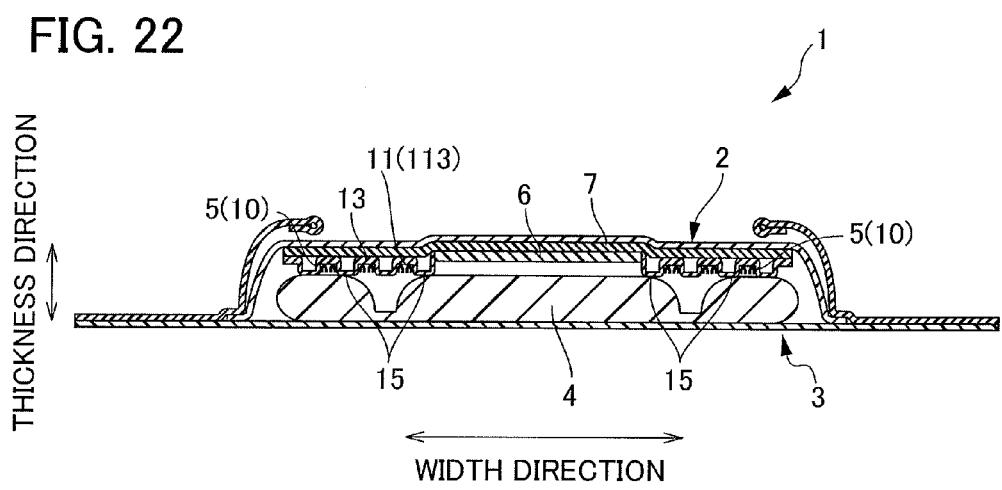
FIG. 22 is a cross-sectional view of an absorbent article using the composite sheet as a second sheet.
Figure 23:
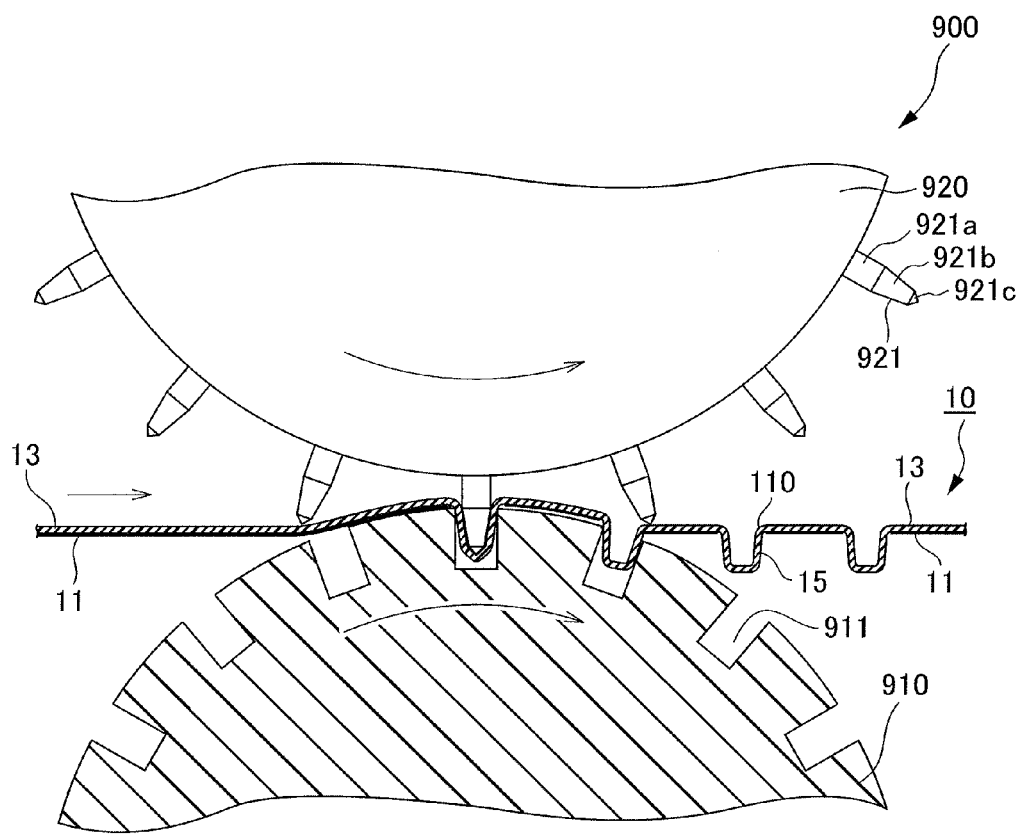
FIG. 23 is a diagram illustrating an embossing roller device.

FIG. 1 is a plan view showing an absorbent article according to an embodiment of the present invention. FIG. 2 is a perspective view showing a composite sheet according to a first embodiment. FIG. 3 is a cross-sectional view of the composite sheet according to the first embodiment. FIG. 4 is a perspective view of a composite sheet according to a second embodiment. FIG. 5 is a cross-sectional view of the composite sheet according to the second embodiment. FIG. 6 is a perspective view of a composite sheet according to a third embodiment. FIG. 7 is a cross-sectional view of the composite sheet according to the third embodiment. FIG. 8 is a perspective view of a composite sheet according to the third embodiment. FIG. 9 is a cross-sectional view of a composite sheet according to the third embodiment. FIG. 10 is a perspective view of the composite sheet according to the fourth embodiment. FIG. 11 is a cross-sectional view of the composite sheet according to the fourth embodiment. FIG. 12 is a perspective view showing a composite sheet according to a fifth embodiment. FIG. 13 is a cross-sectional view of the composite sheet according to the fifth embodiment. FIG. 14 is a cross-sectional view of a composite sheet according to a sixth embodiment. FIG. 15 is a perspective view of the composite sheet according to the sixth embodiment. FIGS. 16A to 16D are diagrams illustrating various projecting regions. FIG. 17 is a cross-sectional view of an absorbent article using the composite sheet as a top sheet. FIG. 18 is a cross-sectional view of an absorbent article using the composite sheet as a top sheet. FIG. 19 is a cross-sectional view of an absorbent article using the composite sheet as a second sheet. FIG. 20 is a cross-sectional view of an absorbent article using the composite sheet as a second sheet. FIG. 21 is a cross-sectional view of an absorbent article using the composite sheet as a second sheet. FIG. 22 is a cross-sectional view of an absorbent article using the composite sheet as a second sheet. FIG. 23 is a diagram illustrating an embossing roller device. FIGS. 24A to 24D are diagrams illustrating a structure of a first roller member and a second roller member in the embossing roller device.

1. Overview

An absorbent article 1 according to an embodiment of the present invention shown in FIG. 1 is an absorbent article having an elongated shape including: a top sheet 2 that is at least partially liquid permeable; a back sheet 3 that is liquid impermeable; and an absorbent core 4 that is liquid retentive and disposed between the top sheet 2 and the back sheet 3. The absorbent article 1 further includes a second sheet 5 that is disposed between the top sheet 2 and the absorbent core 4.

The absorbent article 1 includes a film sheet 11 and a fiber aggregate 13 as the top sheet 2. The top sheet 2 is, for example, a composite sheet including the film sheet 11 and the fiber aggregate 13, the film sheet 11 having a plurality of openings 110 as shown in FIG. 2 and/or a plurality of slits 120 as shown in FIG. 6 formed therein, and the fiber aggregate 13 being layered and disposed on one (a first) side of the film sheet 11 and having a plurality of projecting regions 15 projecting toward another (a second) side of the film sheet 11, which are a part of the fiber aggregate 13 passing through the plurality of openings 110 and/or the plurality of slits 120 as a plurality of through portions.

The composite sheet is preferably disposed such that the fiber aggregate faces a top side of the absorbent article, and the plurality of projecting regions 15 face the absorbent core 4.

In addition, the composite sheet can be disposed as the second sheet 5 of the absorbent article 1. In a case where the composite sheet is disposed as the second sheet 5 of the absorbent article 1, the composite sheet can be disposed so as to direct the plurality of projecting regions 15 either to the top sheet 2 or to the absorbent core 4.

The composite sheet can have various structures in accordance with the functionality desired. For example, the composite sheet can be formed so that at least a portion of a peripheral region of each of the plurality of openings 110 and/or the plurality of slits 120 deforms to stand toward a projecting side of the projecting regions 15, thereby covering at least a portion of a base portion 157 of each of the projecting regions 15. It should be noted that the "base portion 157" is a region in the vicinity of a point where a direction of a side wall 150 of the projecting region 15 extending and a direction of a surface of the fiber aggregate 13 extending cross, and in the vicinity of a side to the fiber aggregate 13 of the side wall 159 of the projecting region 15.

In addition, as shown in FIG. 6, for example, a portion of the film sheet 11 disposed between a predetermined projecting region 15A and a projecting region 15B disposed adjacent thereto in the plurality of projecting regions 15 forms a U-shaped groove extending in a first direction, by continuously deforming in a U-shape projecting toward the fiber aggregate 13.

The U-shaped groove 113 is formed to extend in a straight line or in a curved line in the first direction. For example, as shown in FIG. 6, the U-shaped groove 113 is formed along at least a portion of the side wall 150 of the projecting regions 15. The U-shaped groove 113 is formed to meander in the first direction. As used herein, "meander" indicates that the U-shaped groove is winding, curving along the curved line of the projecting region 15 that is substantially elliptical, and extending along a side edge, which is straight, of the projecting region 15, alternately. In addition, as shown in FIGS. 4 to 7, two U-shaped grooves 113 are formed in parallel between the predetermined projecting region 15A and the projecting region 15B, which is adjacent thereto, in a second direction that is substantially orthogonal to the first direction.

Figure 16B:
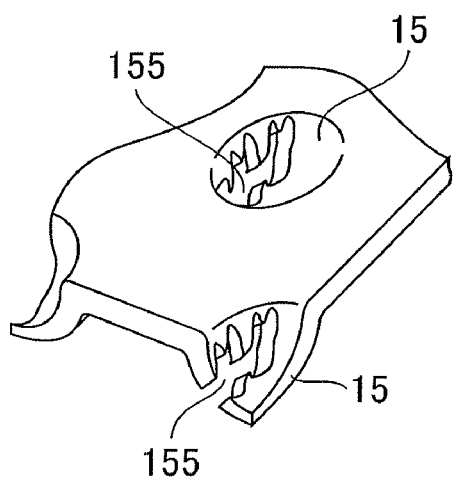
FIG. 16B is a diagram illustrating various projecting regions.
Figure 16C:
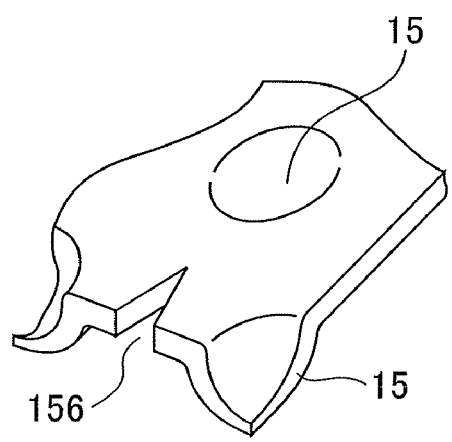
FIG. 16C is a diagram illustrating various projecting regions.
Figure 16D:
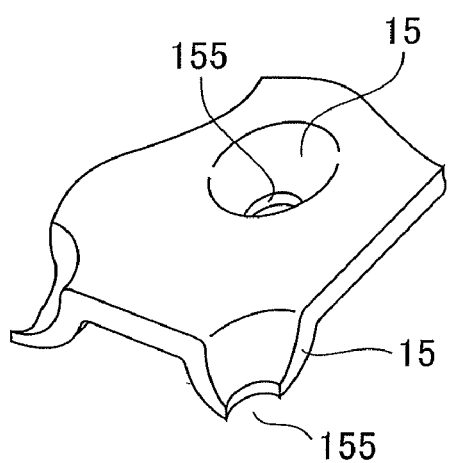
FIG. 16D is a diagram illustrating various projecting regions.

In addition, as shown in FIGS. 16B and 16D, a communicating hole 155 may be formed in the projecting regions 15. The communicating hole 155 can be formed such that a portion of a side (lateral) face 150 of the projecting regions 15 splits up as shown in FIG. 16B, or such that an apex of the projecting regions 15 opens up, as shown in FIG. 16D.

The composite sheet can further include a fiber aggregate including cellulosic fiber on another side of the film sheet.

Here, a method for manufacturing a composite sheet including: a laminating/disposing step of forming a layered sheet by disposing a substantially sheet-shaped fiber aggregate on one side of a predetermined film sheet to be layered; and a projecting region forming step of forming a plurality of projecting regions that project toward another side of the film sheet by pushing through the film sheet from a side of the fiber aggregate opposite to a side to the film sheet, to dislocate portions on the fiber aggregate, by means of a predetermined projecting region forming means, can be exemplified as the method for manufacturing the composite sheet.

Here, the film sheet is preferably a low-elasticity film sheet. In addition, the film sheet is preferably a film sheet with a plurality of openings formed in advance.

More specifically, as shown in FIG. 23, in the projecting region forming step, an embossing roller device 900 as the projecting region forming means includes a first roller member 910 and a second roller member 920. The first roller member 910 is the first member having a flat surface or a curved surface with a plurality of openings 911 formed thereon. The second roller member 920 is the second member having a flat surface or a curved surface with a plurality of projections 921 formed thereon corresponding to the plurality of openings 911. The flat surface or the curved surface, on which the plurality of projections 921 is formed, is disposed so as to face the flat surface or the curved surface of the first roller member 910, on which the plurality of openings 911 is formed.

Figure 24A:
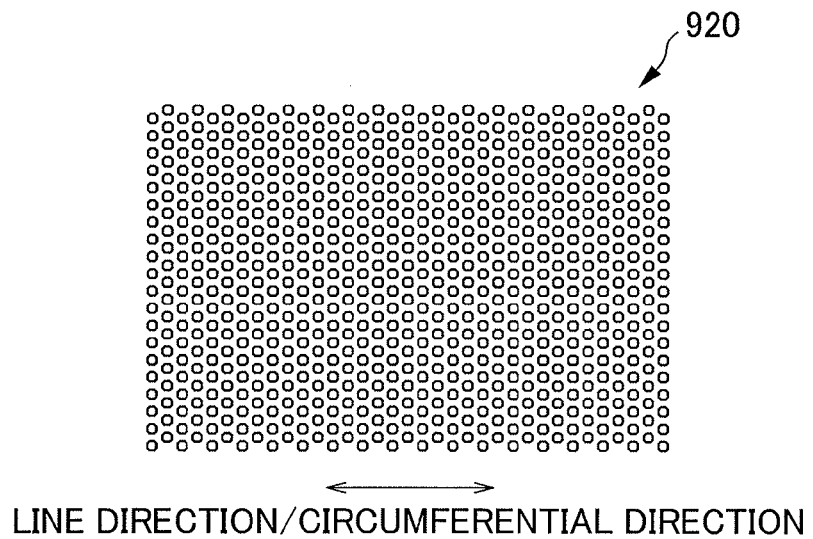
FIG. 24A is a diagram illustrating a structure of a first roller member and a second roller member in the embossing roller device.
Figure 24B:
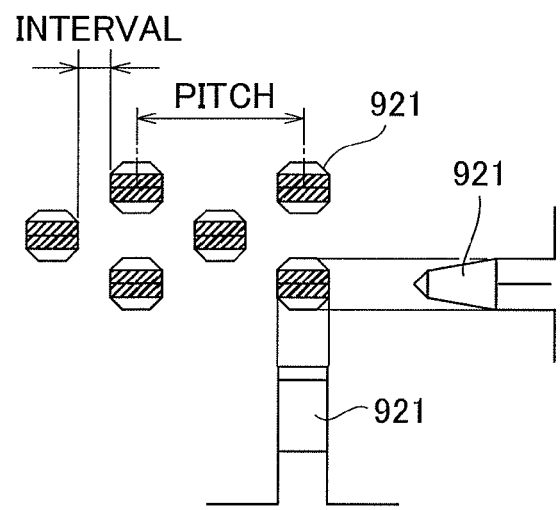
FIG. 24B is a diagram illustrating a structure of the first roller member and the second roller member in the embossing roller device.
Figure 24C:
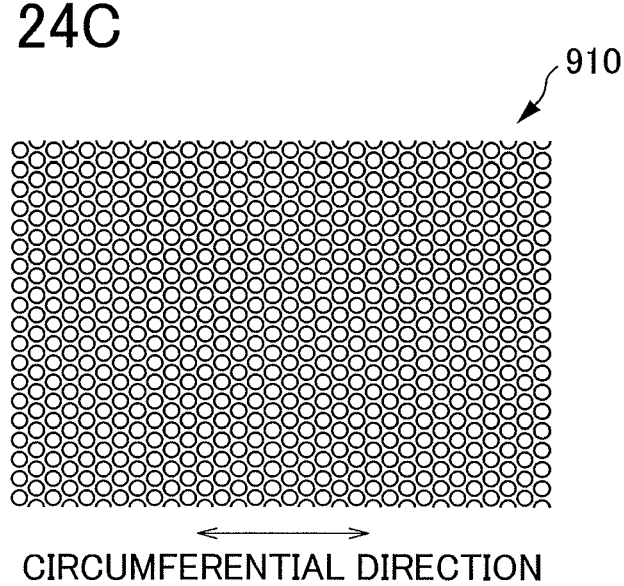
FIG. 24C is a diagram illustrating a structure of the first roller member and the second roller member in the embossing roller device.
Figure 24D:
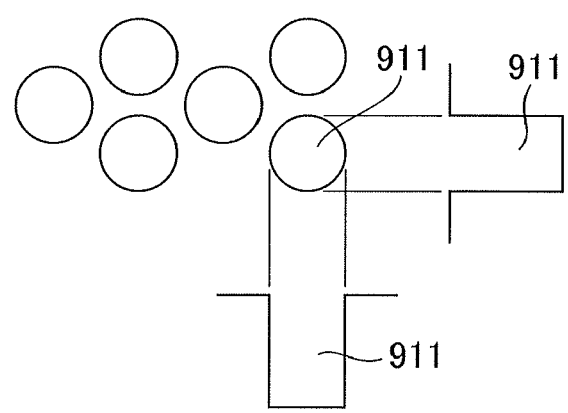
FIG. 24D is a diagram illustrating a structure of the first roller member and the second roller member in the embossing roller device.

An example of a pattern of the openings 911 and the projections 921 on the first roller member 910 and the second roller member 920 of the embossing roller device 900 is shown in FIGS. 24A and 24B.

In a state of being disposed such that a side to the film sheet 11 faces the first roller member 910 and a side to the fiber aggregate 13 faces the second roller member 920, the layered sheet is tucked into the embossing roller device 900, as the projecting region forming means, so that at least a part of the plurality of projections 921 formed on the second roller member 920 engages at least a part of the plurality of openings 911 formed on the first roller member 910, thereby forming a plurality of projecting regions 15 projecting toward the second side, by pushing to dislocate portions on the fiber aggregate 13 by way of the at least a part of the plurality of projections 921.

A draw ratio of the fiber aggregate 13 by the projections 921 is higher than the elasticity of the film sheet 11 in an extension direction by the projections 921. With such a draw ratio, for example, the projections 921 can penetrate the film sheet 11 from one side to another side and project a fiber constituting the fiber aggregate 13 toward the second side of the film sheet 11, thereby forming the projecting regions 15 on the fiber aggregate 13.

In addition, the film sheet 11 is preferably a uniaxially stretched film sheet. With such a film sheet, the abovementioned U-shaped groove and the like can be appropriately formed.

2. Composite Sheet
2.1. First Embodiment
2.1.1. Overall Configuration A composite sheet 10A according to a first embodiment is described hereinafter with reference to FIGS. 2 and 3. As shown in FIG. 2, the composite sheet 10A includes a film sheet 11 on which a plurality of openings 110 is formed, and a fiber aggregate 13 that is disposed to be layered on one side of the film sheet 11. A portion of the fiber aggregate 13 has a plurality of projecting regions 15 that project to another side of the film sheet 11 through the plurality of openings 110. A film sheet on which the openings 110 are formed in advance can be used as the film sheet 11 for the composite sheet.

The projecting regions 15 on the composite sheet 10 can have a height (length in a thickness direction) of 0.3 to 5.0 mm, and more particularly of 0.5 to 2.0 mm. In addition, the projecting regions 15 can have a length in a planar direction (width or diameter) of 0.5 to 10 mm, and more particularly of 1.0 to 5.0 mm. Furthermore, a cross section in the planar direction (direction orthogonal to the thickness direction) of the projecting region 15 can be adjusted to be rectangular, square, circular, elliptical, and the like.

A distance (clearance size) between adjacent projecting regions 15 is, for example, from −5 to 10 mm, and more particularly from −1 to 5 mm. Here, a negative value indicates that the projecting regions 15 overlap each other without a gap, when viewed from a predetermined direction.

An area ratio of the projecting regions 15 in the composite sheet 10A is from 1 to 50%, and preferably from 5 to 30%. The area ratio of the projecting regions 15 can be calculated from a sum of an area of a cross section in the base portion 157 of the projecting regions 15, and a surface area of the composite sheet 10A.

2.1.2. Film Sheet

An opening diameter of the openings 110 provided in advance on the film sheet 11 is, for example, preferably from 0.2 to 2.0 mm, and more preferably from 0.5 to 1.0 mm. An opening area of each of the openings 110 is, for example, preferably from 0.03 to 3 mm$^2$, and more preferably from 0.2 to 0.8 mm$^2$. An opening area ratio of the openings 110 formed on the film sheet 11 is, for example, preferably from 5 to 60%, and more preferably from 10 to 40%. A thickness of the film sheet 11 is, for example, preferably from 10 to 150 μm, and more preferably from 15 to 80 μm. A basis weight of the film sheet 11 is, for example, preferably from 10 to 60 g/m$^2$, and more preferably from 15 to 40 g/m$^2$. An opening forming method for forming the openings 110 on the film sheet 11 is not particularly limited.

2.1.3. Fiber Aggregate

As the fiber aggregate 13, a fiber web and a non-woven fabric can be exemplified. A non-woven fabric formed to be difficult to damage, even in contact with menstrual blood, is preferable. An air-through non-woven fabric is preferable as being low-density and having thermally bonded intersections of fibers, thus easily transferring menstrual blood downwards continuously.

2.1.4. Manufacturing Method

Here, a method for manufacturing the composite sheet including: a laminating/disposing step for forming a layered sheet by disposing a substantially sheet-shaped fiber aggregate 13 to be layered on one side of the film sheet 11; and a projecting region forming step for forming a plurality of projecting regions 15 that project toward another side of the film sheet 11 by pushing through the film sheet 11 from a side of the fiber aggregate 13 opposite to a side to the film sheet 11, to dislocate portions on the fiber aggregate 13, by way of a predetermined projecting region forming means, can be exemplified as the method for manufacturing the composite sheet 10A.

As a method for forming the projecting regions 15, an embossing method and a needling method can be exemplified. For example, in consideration of mass production and shape holding of the fiber aggregate 13, an embossing method is preferable for forming the projecting regions 15.

More specifically, first, a layered sheet is formed by disposing and adhering the fiber aggregate 13 on one side of the film sheet 11 by way of a predetermined adhesive, as shown in FIG. 23. Subsequently, the plurality of projecting regions 15 are formed on the layered sheet according to the embossing method by way of the embossing roller device 900 as the projecting region forming means.

The embossing roller device 900, as the projecting region forming means, includes a first roller member 910 and a second roller member 920. The first roller member 910 is the first member having a curved surface with a plurality of openings 911 formed thereon. The second roller member 920 is the second member having a curved surface with a plurality of projections 921 formed thereon corresponding to the plurality of openings 911. The curved surface is disposed so as to face the curved surface of the first roller member 910, on which the plurality of openings 911 is formed. Here, in the embossing roller device 900, the plurality of projections and the plurality of openings are formed on a cylindrical roller; however, the present invention is not limited thereto, and the projections and the openings can be formed on a flat surface of a planar member.

In a state of being disposed such that a side to the film sheet 11 faces the first roller member 910 and a side to the fiber aggregate 13 faces the second roller member 920, the layered sheet is tucked into the embossing roller device 900, as the projecting region forming means, so that at least a part of the plurality of projections 921 formed on the second roller member 920 engages at least a part of the plurality of openings 911 formed on the first roller member 910, thereby forming a plurality of projecting regions 15 projecting toward another side, by pushing to dislocate portions on the fiber aggregate 13 by way of the at least a part of the plurality of projections 921.

Here, as a cross-sectional shape of the projections 921 formed on the second roller member 920, a rectangular shape, a square shape, a circular shape, an elliptical shape, and the like in a direction vertical to a radial direction of the second roller member 920 can be exemplified. A cross section of the openings 911 formed on the first roller member 910 is not particularly limited so far as being larger than the cross section of the projections 921. As the cross-sectional shape of the openings 911, continuous wave, intermittent wave and the like can be exemplified in addition to a rectangular shape, a square shape, a circular shape, and an elliptical shape.

As a cross-sectional shape of the projections 921 in the vicinity of an apex thereof, a rectangular shape, a tapered trapezoidal shape, a triangle shape, a pin shape, an arc, and the like can be exemplified. Particularly, in a case where the projecting regions 15 are formed by splitting the film sheet 11 while not splitting the fiber aggregate 13 and tucking the fiber aggregate 13 into the openings 911, as shown in FIG. 24B, a shape with an apex, that is a triangle when viewed from a line direction and that is rectangular when viewed from a direction orthogonal to the line direction, can be exemplified as a shape of the projections 921. The projections 921 on the second roller member 920 can be arranged, for example, in a reticular pattern or in a zigzag pattern, in a circumferential direction of the second roller member 920.

The openings 110 and slits can be provided in portions in which the projecting regions 15 are provided, on the film sheet 11 in advance, so that the fiber aggregate 13 can easily penetrate a portion of the film sheet 11 in projecting region formation processing. In addition, the film sheet 11 can be further widened to such a degree that the film sheet 11 is not broken, in order to lower the elasticity thereof. Furthermore, a low-elasticity film sheet can be used as the film sheet 11.

2.1.5. Example

An example of the composite sheet 10A according to the present embodiment is described hereinafter.

The film sheet 11 is a sheet mainly composed of LLPE and LDPE, into which titanium oxide and a hydrophilic oil solution are blended and of which the basis weight is adjusted to 25 g/m$^2$. Openings are formed on the sheet by way of a tentering processing, with an opening diameter of 0.5 mm, an opening area of 0.2 mm$^2$, and an opening area ratio of 20%.

The fiber aggregate 13 that is disposed to be layered on one side of the film sheet 11 is an air-through non-woven fabric made with 100% sheath-core fiber of HDPE and PET, with a basis weight of 30 g/m$^2$, average fineness of 2.2 dtex, and average fiber length of 51 mm, and 4% by weight of titanium oxide blended into a core and coated with the hydrophilic oil solution.

The projecting regions 15 are formed by way of the embossing roller device 900 shown in FIG. 23, according to the abovementioned manufacturing method. The projections 921 on the embossing roller device 900 have a hexagonal cross-section in a planar direction, and a shape thereof changes as approaching an apex. For example, the projection 921 has different shapes in a base portion 921a, a middle portion 921b, and an apex portion 921c. In other words, in a case where the projection 921 is seen from a width direction, the base portion 921a has a rectangular shape of 1.9 mm in width and 2.0 mm in height, the middle portion 921b has a trapezoidal shape of 2.5 mm in length in the line direction and with a taper of 20°, and the apex portion 921c has a triangle shape of 0.5 mm in height and with a taper of 45°. In addition, when seen from a direction orthogonal to the width direction, the projection 921 has a rectangular shape of 1.75 mm in width and 5.0 mm in height.

The projections 921 are arranged in a zigzag pattern in a circumferential direction on the second roller member 920. The projections 921 on the second roller member 920 are arranged at pitches of 3.0 mm and intervals of 1.25 mm in a circumferential direction (a direction of a manufacturing line), and at pitches of 3.5 mm and intervals of −0.5 mm in a width direction. The interval in the width direction is an interval between projections 921 that are adjacent in the width direction, in other words, an interval in the width direction between the projection 921 and the projection 921 in FIG. 23.

The openings 911 formed on a surface of the first roller member 910 have a substantially cylindrical shape. A plurality of cylindrical openings 911, of 2.0 mm in diameter and 6.0 mm in height, is formed on a surface of the first roller member 910. An arrangement of the openings 911 on the first roller member 910 is in a zigzag pattern corresponding to an arrangement of the projections 921 on the second roller member 920.

Here, an interval between the first roller member 910 and the second roller member 920 is 0.5 mm. The first roller member 910 and the second roller member 920 performs the projecting region formation processing in a state of being heated to 60° C. (333.15 K).

In the composite sheet 10A that is manufactured according to the abovementioned conditions and the abovementioned manufacturing method, the projecting regions 15 are 2.0 mm in height (length in a thickness direction of the composite sheet 10), 1.7 mm in length in a width direction that is orthogonal to the direction of the manufacturing line, and 1.5 mm in length in the line direction.

A cross-sectional shape of the projecting region 15 in a planar direction is elliptical. An interval between adjacent projecting regions 15 is 1.2 mm in the line direction, and −0.5 mm in the width direction that is orthogonal to the line direction. In addition, an area ratio of the projecting regions 15 is 10%.

As described later, the composite sheet 10A according to the present embodiment can be used as the top sheet 2 of the absorbent article 1. In addition, the composite sheet 10A according to the present embodiment can also be used as the second sheet 5 of the absorbent article 1.

In a case where the composite sheet 10A according to the present embodiment is used as the top sheet 2 or the second sheet 5, for example, the absorbent article 1 of a superior concealing property of menstrual blood and superior backset (rewet) suppressing ability can be obtained.

2.2. Second Embodiment 2.2.1. Overall Configuration

A composite sheet 10B according to a second embodiment is described hereinafter with reference to FIGS. 4 and 5. Unlike the composite sheet 10A according to the first embodiment, a film sheet 11, on which openings 110 are not formed in advance, is used in the composite sheet 10B according to the present embodiment. In other words, in the present embodiment, projecting portions 15 are formed while forming slits by splitting portions of the film sheet 11, in the projecting region forming step.

More specifically, as shown in FIG. 4 or 5, the composite sheet 10B according to the present embodiment is a composite sheet that includes the film sheet 11 and the fiber aggregate 13, the film sheet 11 having a plurality of slits 120 formed therein, and the fiber aggregate 13 being disposed to be layered on one side of the film sheet 11 and having a plurality of projecting regions 15 projecting toward another side of the film sheet 11, which are a part of the fiber aggregate 13 passing through the plurality of slits 120.

The film sheet 11 in the composite sheet 10B is disposed such that at least a portion of a peripheral region of each of the plurality of slits 120 deforms to stand toward a projecting side of the projecting regions 15, thereby covering at least a portion of a base portion 157 of each of the plurality of projecting regions 15.

In addition, a portion of the film sheet 11 disposed between a predetermined projecting region 15A and a projecting region 15B disposed adjacent thereto in the plurality of projecting regions 15 forms a U-shaped groove 113 extending in a line direction, which is a first direction, by continuously deforming to a U-shape projecting toward the fiber aggregate 13.

The U-shaped groove 113 is formed to extend straight in a line direction. In addition, the U-shaped groove 113 is formed along a portion of the side wall 150 of the projecting regions 15.

Furthermore, two U-shaped grooves 113 are formed in parallel between the predetermined projecting region 15A and the projecting region 15B that is adjacent thereto in a second direction that is substantially orthogonal to the line direction.

The slits that are formed by splitting the film sheet 11 are, for example, from 0.2 to 2.0 mm, and particularly from 0.5 to 1.0 mm, in width. An area ratio of the fiber aggregate 13 that is exposed by passing through the slits is preferably from 5 to 80%, and more preferably from 10 to 50%.

A film sheet 11 having elasticity lower than a draw ratio that is obtained by an embossing finish in the projecting region forming step can be used as the film sheet 11.

2.2.2. Manufacturing Method

A manufacturing method for the composite sheet 10B according to the present embodiment is substantially similar to that of the composite sheet 10A according to the first embodiment. Conditions and the like that are different from the manufacturing method of the composite sheet 10A according to the first embodiment are mainly described hereinafter.

Projections 921 formed on a surface of the second roller member 920 of the embossing roller device 900 are arranged in a zigzag pattern as in the first embodiment; however, an interval between adjacent projections 921 in a width direction that is orthogonal to the circumferential direction of the second roller member 920 is greater than that of the first embodiment.

In addition, the openings 911 formed on a surface of the first roller member 910 are formed so as to meander in the circumferential direction, following the projections 921.

The film sheet 11 used for the composite sheet 10B has an elasticity in the width direction that is orthogonal to the line direction, which is lower than the draw ratio by the projections 921. As such a low-elasticity film sheet 11, a film sheet 11, which is provided with high stretchability by a T-die method or an inflation method, can be exemplified. More particularly, as a film sheet 11 having a low elasticity in the width direction, a uniaxially stretched film sheet 11, which is provided with a high stretchability in the line direction, can be exemplified.

The film sheet 11 is preferably a sheet composed of thermoplastic resins such as linear low-density polyethylene (LLPE), low-density polyethylene (LDPE), high-density polyethylene (HDPE), polypropylene (PP) and polyethylene terephthalate (PET), and more preferably a film sheet 11 mainly composed of HDPE. For example, the film sheet 11 mainly composed of HDPE is preferable since the film sheet has superior shape holding properties in the composite sheet 10B. In addition, a basis weight of the film sheet 11 is preferably 25 g/m$^2$.

Here, in a case where the projections 921 are formed in a reticular pattern, not in a zigzag pattern, in the circumferential direction, only a single U-shaped groove 113 is formed between adjacent projecting regions 15.

In addition, the first embodiment has shown that the film sheet 11 has two peaks between the projecting regions; however, in a case where embossed convex portions are arranged in a reticular pattern, not in a zigzag pattern, the film sheet 11 is formed so as to have a single peak.

Here, the composite sheet 10B according to the present embodiment can be used as the top sheet 2 of the absorbent article 1. In addition, the composite sheet 10B according to the present embodiment can also be used as the second sheet 5 of the absorbent article 1.

For example, by disposing the composite sheet 10B according to the present embodiment such that a side on which the film sheet 11 is disposed faces the absorbent core 4, the U-shaped groove 113 can appropriately suppress the backset of liquid from the absorbent core 4.

In a case where the composite sheet 10B according to the present embodiment is used as the top sheet 2 or the second sheet 5, for example, an absorbent article 1 of superior concealing property for menstrual blood and superior rewet suppressing ability can be obtained.

2.3. Third Embodiment 2.3.1. Overall Configuration

A composite sheet 10C according to a third embodiment is described hereinafter with reference to FIGS. 6 to 9. The composite sheet 10C according to the present embodiment is a composite sheet in which the projecting regions 15 are formed at smaller intervals in the width direction than in the composite sheet 10B according to the second embodiment.

More specifically, as shown in FIGS. 6 to 9, the composite sheet 10C according to the present embodiment is a composite sheet that includes the film sheet 11 and the fiber aggregate 13, the film sheet 11 having a plurality of slits 120 formed therein, and the fiber aggregate 13 being disposed to be layered on one side of the film sheet 11 and having a plurality of projecting regions 15 projecting toward another side of the film sheet 11, which are a part of the fiber aggregate 13 passing through the plurality of slits 120.

The film sheet 11 in the composite sheet 10C is disposed such that at least a portion of a peripheral region of each of the plurality of slits 120 deforms to stand toward a projecting side of the projecting regions 15, thereby covering at least a portion of a base portion 157 of each of the plurality of projecting regions 15.

In addition, a portion of the film sheet 11 disposed between a predetermined projecting region 15A and a projecting region 15B disposed adjacent thereto in the plurality of projecting regions 15 forms a U-shaped groove extending in a line direction, by continuously deforming to a U-shape projecting toward the fiber aggregate 13.

The plurality of projecting regions 15 on the composite sheet 10C is formed to have an elliptical cross section in a planar direction and in a zigzag pattern in the planar direction. The plurality of projecting regions 15 on the composite sheet 10C is formed at smaller intervals than in the composite sheet 10B according to the second embodiment. More specifically, an interval between a predetermined projecting region 15A and a projecting region 15B that is adjacent thereto is smaller than a length in a width direction of the projecting region 15A or the projecting region 15B. In other words, an interval between the projecting region 15A and the projecting region 15B is smaller than a length in a width direction of a projecting region 15C that is adjacent to the projecting region 15A and the projecting region 15B in the line direction.

The U-shaped groove 113 formed between the adjacent projecting regions 15 is formed to meander in a line direction.

Furthermore, two U-shaped grooves are formed in parallel between the predetermined projecting region 15A and the projecting region 15B that is adjacent thereto.

The width of the slits that are formed by splitting the film sheet 11 is, for example, preferably from 0.2 to 2.0 mm, and more preferably from 0.5 to 1.0 mm. An area ratio of the fiber aggregate 13 that is exposed by passing through the slits is preferably from 5 to 80%, and more preferably from 10 to 50%.

In addition, the film sheet 11 having elasticity lower than a draw ratio that is obtained by an embossing finish in the projecting region forming step.

Here, in the composite sheet 10C according to the present embodiment, since portions in the film sheet 11 form the U-shaped grooves 113 that meander in the line direction, external pressure applied in the thickness direction, for example, is not concentrated only on the projecting regions 15. In addition, since the U-shaped grooves 113 are formed to meander in the line direction, the external pressure applied thereon is also distributed, thereby preventing the U-shape of the U-shaped groove 113 from opening and being crushed.

2.3.2. Manufacturing Method

A manufacturing method for the composite sheet 10C according to the present embodiment is substantially similar to that of the composite sheet 10B according to the second embodiment. Conditions and the like that are different from the manufacturing method of the composite sheet 10B according to the second embodiment are mainly described hereinafter.

Projections 921 formed on a surface of the second roller member 920 of the embossing roller device 900 are arranged in a zigzag pattern in a circumferential direction as in the second embodiment; however, an interval between adjacent projections 921 in a width direction that is orthogonal to the circumferential direction of the second roller member 920 is smaller than that of the second embodiment. The interval in the width direction is the same as the abovementioned interval between the adjacent projecting regions 15.

The openings 911 are formed on a surface of the first roller member 910 in a zigzag pattern in the circumferential direction, corresponding to the projections 921.

The film sheet 11 used for the composite sheet 10C has an elasticity in the width direction, which is orthogonal to the line direction, which is lower than the draw ratio by the projections 921. As such a low-elasticity film sheet 11, a film sheet 11, which is provided with a high stretchability by a T-die method or an inflation method, can be exemplified. More particularly, as a film sheet 11 having low elasticity in the width direction, a uniaxially stretched film sheet 11, which is provided with a high stretchability in the line direction, can be exemplified.

The film sheet 11 is preferably a sheet composed of thermoplastic resins such as LLPE, LDPE, HDPE, PP and PET, and more preferably a film sheet 11 mainly composed of HDPE. For example, the film sheet 11 mainly composed of HDPE is preferable since the film sheet has a superior shape holding properties in the composite sheet 10C. In addition, a basis weight of the film sheet 11 is preferably 25 g/m$^2$.

Here, the composite sheet 10C according to the present embodiment can be used as the top sheet 2 of the absorbent article 1. In addition, the composite sheet 10C according to the present embodiment can also be used as the second sheet 5 of the absorbent article 1.

For example, in a case where the composite sheet 10C according to the present embodiment is used as the second sheet 5 of the absorbent article 1, the composite sheet 10C can be disposed so as to cover one entire side of the absorbent core 4, as shown in FIG. 19. In such a case, the composite sheet 10C can be disposed so as to direct the projecting regions 15 either to the top sheet or to the absorbent core 4. Here, in order to smoothly transfer liquid such as menstrual blood discharged on a surface from the top sheet 2, it is preferable to dispose the projecting regions 15 to face the absorbent core 4 so that the fiber aggregate 13 faces the top sheet 2. In other words, the composite sheet 10C is preferably disposed such that the fiber aggregate 13 in the composite sheet 10C is in contact with the top sheet 2.

In addition, as shown in FIG. 20, the composite sheet 10C can be disposed on both sides in the width direction of the absorbent article 1. The composite sheet 10C can suppress side leakage even in a case where liquid such as menstrual blood runs in the width direction of the absorbent article 1, by drawing the liquid in. As described above, the composite sheet 10C can be disposed in both side portions in the width direction of the absorbent article 1, as a second sheet. In such a case, the composite sheet 10C can be disposed so as to direct the projecting regions 15 either to the top sheet or to the absorbent core 4. In addition, as described above, in order to smoothly transfer liquid such as menstrual blood discharged on a surface of the top sheet 2, the composite sheet 10C is preferably disposed such that the projecting regions 15 face the absorbent core 4 and the fiber aggregate 13 faces the top sheet 2. In other words, the composite sheet 10C is preferably disposed such that the fiber aggregate 13 in the composite sheet 10C is in contact with the top sheet 2.

2.3.3. Evaluation

A liquid drawing ability and backset (rewet) suppressing ability are hereinafter described, in a case where the composite sheet 10C is disposed so as to direct the projecting regions 15 to the absorbent core and the fiber aggregate 13 to the top sheet. A result of comparative evaluation for a liquid drawing ability and a liquid backset suppressing ability is shown below, for the composite sheet 10C, a conventional non-woven fabric (Comparative Example 1) and a film sheet with openings formed thereon (Comparative Example 2), which are used as a second sheet. The term "liquid drawing ability" refers to a property, in a case where liquid such as menstrual blood is dropped on a predetermined portion on the sheet, whereby a sheet lets through a liquid and guides the liquid to an absorbent core disposed below the sheet.

Comparative Example 1 a non-woven fabric made with 100% sheath-core fiber of HDPE and PET, with a basis weight of 20 g/m$^2$, average fineness of 2.2 dtex, average fiber length of 51 mm, and 4% by mass of titanium oxide blended into a core, and which is coated with a hydrophilic oil solution.

Comparative Example 2 a film sheet mainly composed of LLPE and LDPE of 25 g/m$^2$ in basis weight, into which titanium oxide and a hydrophilic oil solution are blended, and on which openings are formed by way of an opening processing. Here, an opening diameter is 0.6 mm, an opening area is 0.28 mm$^2$, and an opening area ratio is 22%.

A residual liquid ratio (liquid drawing ability) and a liquid backset ratio (rewet suppressing ability) were measured by a method described later, in a case where the composite sheet 10C, the comparative example 1, and the comparative example 2 were used as a second sheet, with the projecting regions 15 facing the absorbent core and the fiber aggregate 13 facing the top sheet. Measurement results of the residual liquid ratio and the liquid backset ratio are as follows.

Composite Sheet 10C: residual liquid ratio on the top sheet: 2.3%, liquid backset ratio: 4.8%

Comparative Example 1: residual liquid ratio on the top sheet: 2.1%, liquid backset ratio: 12.8%

Comparative Example 2: residual liquid ratio on the top sheet: 4.4%, liquid backset ratio: 10.9%

The abovementioned results show that the composite sheet 10C, which was used as a second sheet, had a superior liquid drawing ability and a liquid backset (rewet) suppressing ability.

In addition, as described above, in a case where the composite sheet 10c according to the present embodiment is used as the top sheet 2 or the second sheet 5, for example, an absorbent article 1 of superior concealing property for menstrual blood and superior backset (rewet) suppressing ability can be obtained.

2.4. Fourth Embodiment

A composite sheet 10D according to a fourth embodiment is described hereinafter with reference to FIGS. 10 and 11. The composite sheet 10D according to the present embodiment is different from the composite sheet 10C according to the third embodiment in that a film sheet 11 on which openings 110 are formed in advance is used. The openings 110 that are formed in the film sheet 11 of the composite sheet 10D are formed in a circular shape of substantially the same diameter as the diameter of the projecting regions 15 in a planar direction. In addition, the projecting regions 15 are different from the projecting regions 15 of the composite sheet 10C according to the third embodiment in a cross-sectional shape thereof.

More specifically, as shown in FIGS. 10 and 11, the composite sheet 10D according to the present embodiment is a composite sheet that includes the film sheet 11 and the fiber aggregate 13, the film sheet 11 having a plurality of openings 110, which have a circular shape of substantially the same diameter as that of the projecting regions 15 in a planar direction, formed therein, and the fiber aggregate 13 being disposed to be layered on one side of the film sheet 11 and having a plurality of projecting regions 15 projecting toward another side of the film sheet 11, which are a part of the fiber aggregate 13 passing through the plurality of openings 110.

The film sheet 11 in the composite sheet 10D is substantially planar as a whole. In other words, a portion of the film sheet 11 disposed between a predetermined projecting region 15A and a projecting region 15B disposed adjacent thereto in the plurality of projecting regions 15 is maintained to be planar without being deformed.

The plurality of projecting regions 15 on the composite sheet 10D are formed in a zigzag pattern in the planar direction. The plurality of projecting regions 15 on the composite sheet 10D are formed at small intervals as in the composite sheet 10C according to the third embodiment.

Here, the composite sheet 10D according to the present embodiment can be used as the top sheet 2 of the absorbent article 1. In addition, the composite sheet 10D according to the present embodiment can also be used as the second sheet 5 of the absorbent article 1.

For example, in a case where the composite sheet 10D according to the present embodiment is used as the second sheet 5 of the absorbent article 1, the composite sheet 10D can be disposed so as to cover one entire side of the absorbent core 4, as shown in FIG. 19. In such a case, the composite sheet 10D can be disposed so as to direct the projecting regions 15 either to the top sheet 2 or to the absorbent core 4. Here, in order to smoothly transfer liquid such as menstrual blood discharged on a surface of the top sheet 2, the composite sheet 10D is preferably disposed such that the projecting regions 15 face the absorbent core 4 and the fiber aggregate 13 faces the top sheet 2. In other words, the composite sheet 10D is preferably disposed such that the fiber aggregate 13 in the composite sheet 10D is in contact with the top sheet 2.

In addition, as shown in FIG. 20, the composite sheet 10D can be disposed on both sides in the width direction of the absorbent article 1. The composite sheet 10D can suppress side leakage even in a case where liquid such as menstrual blood runs in the width direction of the absorbent article 1, by drawing the liquid in. As described above, the composite sheet 10D can be disposed in both side portions in the width direction of the absorbent article 1, as a second sheet. In such a case, the composite sheet 10D can be disposed so as to direct the projecting regions 15 either to the top sheet 2 or to the absorbent core 4. In addition, as described above, in order to smoothly transfer liquid such as menstrual blood discharged on a surface of the top sheet 2, the composite sheet 10D is preferably disposed such that the projecting regions 15 face the absorbent core 4 and the fiber aggregate 13 faces the top sheet 2. In other words, the composite sheet 10D is preferably disposed such that the fiber aggregate 13 in the composite sheet 10D is in contact with the top sheet 2.

In a case where the composite sheet 10D according to the present embodiment is used as the top sheet 2 or the second sheet 5, for example, the absorbent article 1 of superior concealing property for menstrual blood and superior backset (rewet) suppressing ability can be obtained.

2.5. Fifth Embodiment

A composite sheet 10E according to a fifth embodiment is described hereinafter with reference to FIGS. 12 and 13. The composite sheet 10E according to the present embodiment is a composite sheet in which the film sheet 11 disposed between the projecting regions 15 in the composite sheet 10D according to the fourth embodiment is deformed to cover a base portion 157 of the projecting regions 15. The film sheet 11 is preferably formed so as to cover an entirety of the base portion of each of the plurality of projecting regions 15.

More specifically, the film sheet 11 in the composite sheet 10E is disposed such that at least a portion of a peripheral region of each of the plurality of openings 110 deforms to stand toward a projecting side of the projecting regions 15, thereby covering at least a portion of a base portion 157 of each of the plurality of projecting regions 15.

Since the film sheet 11 is thus disposed such that at least a portion of the projecting regions 15 in the base portion 157 deforms to stand toward a projecting side of the projecting regions 15, thereby covering at least a portion of a base portion 157 of each of the plurality of projecting regions 15, the projecting regions 15 are not easily crushed by, for example, an external pressure applied in a thickness direction, and easily recover even if crushed.

The plurality of projecting regions 15 on the composite sheet 10E is formed to have an elliptical cross section in a planar direction and in a zigzag pattern.

Differences from the manufacturing method of the composite sheet 10D according to the fourth embodiment are mainly described hereinafter.

First, before processing by the embossing roller device shown in FIG. 23, the film sheet 11 and the fiber aggregate 13 are joined to each other by an adhesive. Since a degree of freedom of the film sheet 11 depends on the fiber aggregate 13, deformation of the film sheet 11 disposed between a predetermined projecting region 15A and a projecting region 15B that is adjacent thereto, which are to be formed, can be suppressed by joining the film sheet 11 with the fiber aggregate 13.

More specifically, the film sheet 11 disposed between the projecting region 15A and the projecting region 15B becomes hard to deform into a U-shape. Consequently, the film sheet 11 disposed in a base portion 157 of the projecting regions 15 formed by the projections 921 deforms to stand toward a projecting side of the projecting regions 15, thereby covering the base portion 157 of the projecting regions 15.

In more detail, the openings 110 are formed by the projections 921 splitting portions of the film sheet 11, and a periphery of the openings 110 deforms to stand toward the projecting side of the projecting regions 15 that are formed with fibers constituting the fiber aggregate 13. In addition, the film sheet 11 is formed such that the periphery of the openings 110 thereon covers the base portion 157 of the projecting regions 15.

In a case where the film sheet 11 and the fiber aggregate 13 are joined with each other by an adhesive, a coating quantity and a coating pattern that can lower the degree of freedom of the film sheet 11 can be chosen. For example, a hot melt adhesive is applied to the fiber aggregate 13 by way of a coating method such as spiral coating, coater coating, curtain coater coating, or summit gun coating, and the film sheet 11 can be laid thereon. In particular, it is preferable that an adhesive is applied by coater coating with a basis weight of 5 to 50 g/m$^2$.

In consideration of a case where an adhesive effuses, a heat sensitive adhesive that has no tackiness at that point is preferable. For example, as such an adhesive, a melt-mixture of 5% to 25% of SEBS, 40% to 60% of alicyclic saturated hydrocarbon, 1% to 10% of aromatic denatured terpene, and 15% to 35% of additive can be exemplified.

Here, the composite sheet 10E according to the present embodiment can be used as the top sheet 2 of the absorbent article 1. In addition, the composite sheet 10E according to the present embodiment can also be used as the second sheet 5 of the absorbent article 1.

In a case where the composite sheet 10E according to the present embodiment is used as the second sheet 5 of the absorbent article 1, the composite sheet 10E can be disposed so as to cover one entire side of the absorbent core 4, as shown in FIG. 19. In such a case, the composite sheet 10E can be disposed so as to direct the projecting regions 15 either to the top sheet or to the absorbent core 4. Here, in order to smoothly transfer liquid such as menstrual blood discharged on a surface of the top sheet 2, as described above, the composite sheet 10E is preferably disposed such that the projecting regions 15 face the absorbent core 4 and the fiber aggregate 13 faces the top sheet 2. In other words, the composite sheet 10E is preferably disposed such that the fiber aggregate 13 in the composite sheet 10E is in contact with the top sheet 2.

In addition, as shown in FIG. 20, the composite sheet 10E can be disposed on both sides in the width direction of the absorbent article 1. The composite sheet 10E can suppress side leakage even in a case where liquid such as menstrual blood runs in the width direction of the absorbent article 1, by drawing the liquid in. As described above, the composite sheet 10E can be disposed in both side portions in the width direction of the absorbent article 1, as a second sheet. In such a case, the composite sheet 10E can be disposed so as to direct the projecting regions 15 either to the top sheet 2 or to the absorbent core 4. In addition, as described above, in order to smoothly transfer liquid such as menstrual blood discharged on a surface of the top sheet 2, the composite sheet 10E is preferably disposed such that the projecting regions 15 face the absorbent core 4 and the fiber aggregate 13 faces the top sheet 2. In other words, the composite sheet 10E is preferably disposed such that the fiber aggregate 13 in the composite sheet 10E is in contact with the top sheet 2.

In a case where the composite sheet 10E according to the present embodiment is used as the top sheet 2 or the second sheet 5, for example, an absorbent article 1 of superior concealing property for menstrual blood and superior rewet suppressing ability can be obtained.

2.7. Sixth Embodiment

A composite sheet 10G according to a sixth embodiment is described hereinafter with reference to FIGS. 14 and 15. The composite sheet 10G according to the present embodiment is a composite sheet formed by further arranging a fiber aggregate 17 including cellulosic fiber on a side of the composite sheet 20C according to the third embodiment on which the film sheet 11 is disposed. In other words, the composite sheet 10G has a layered structure in which the film sheet 11 is sandwiched by the fiber aggregate 13 and the fiber aggregate 17 including cellulosic fiber.

The fiber aggregate 17 including cellulosic fiber is preferably mainly composed of cellulosic liquid hydrophilic fibers such as pulps, chemical pulps, rayon, acetate, natural cotton, and the like. In addition to the cellulosic fiber, thermoplastic resin fiber can be blended in order to improve the strength of the non-woven fabric. A ratio of the cellulosic fiber and the thermoplastic resin fiber is, for example, in a range of 100:0 to 50:50.

The fiber aggregate 17 including cellulosic fiber can be a non-woven fabric. Bonding methods and the like for such a non-woven fabric are as described above. Here, since cellulosic fibers are short fibers, a wet web forming method is preferable for lower elasticity, and a so-called tissue, which is highly productive and inexpensive, is more preferable.

As the composite sheet 10G according to the present embodiment, an air-through non-woven fabric of 30 g/m$^2$ in basis weight used in the first embodiment, a uniaxially stretched film sheet 11 mainly composed of HDPE of 25 g/m$^2$ in basis weight, and a tissue of 18 g/m$^2$ in basis weight on the lowermost side, which are joined with each other by a hot-melt adhesive of 5 g/m$^2$ that is disposed in between by spiral coating, and then processed by the embossing roller device 900 in the second embodiment in order to form a plurality of projecting regions 15, can be exemplified.

Here, the composite sheet 10G according to the present embodiment can be used as the top sheet 2 of the absorbent article 1. In addition, the composite sheet 10G according to the present embodiment can also be used as the second sheet 5 of the absorbent article 1.

For example, as shown in FIGS. 17 and 18, the composite sheet 10G according to the present embodiment can be used as the top sheet 2 of the absorbent article 1. The composite sheet 10G is preferably disposed such that the projecting regions 15 face the absorbent core 4, as shown in FIG. 18. In such a case, liquid such as menstrual blood discharged onto the fiber aggregate 13 can be appropriately transferred to a side to the absorbent core 4. Even if the liquid once absorbed by the absorbent core 4 is about to return under pressure, the liquid makes contact with the fiber aggregate 17 that disperses the liquid in a line direction. Furthermore, the film sheet 11 (for example, the U-shaped groove 113) disposed thereabove, covering the absorbent core 4, also suppresses backset of the liquid toward the fiber aggregate 13.

In a case where the composite sheet 10G according to the present embodiment is used as the top sheet 2 or the second sheet 5, for example, the absorbent article 1 of superior concealing property for menstrual blood and superior rewet suppressing ability can be obtained.

2.7. Others

The projecting regions 15 are described in more detail hereinafter with reference to FIGS. 16A to 16D. The projecting regions 15 shown in FIG. 16A communicate one side to another side of the film sheet (not shown). For example, in a case where a composite sheet is disposed as a second sheet such that the projecting regions 15 face an absorbent core (not shown), a top sheet (not shown) is communicated with the absorbent core via the projecting regions 15. In addition, since a density of the projecting regions 15 becomes higher as approaching an apex thereof, liquid such as menstrual blood can be quickly transferred from a top sheet to an absorbent core.

To form the projecting regions 15 as shown in FIG. 16A, a fiber aggregate of a high elasticity is preferably used, for example. As such a fiber aggregate, a fiber web and a non-woven fabric with loose entanglement or adhesion between fibers can be exemplified. Such a fiber aggregate can be obtained by adjusting the bonding (thermal bonding, needle punch, chemical bonding, and spun lace).

More specifically, by taking the air-through non-woven fabric of 30 g/m², used in the first embodiment, for example, although a heat treatment temperature is generally set to around +/−10° C. of a melting point of a sheath component, an air-through non-woven fabric of loose adhesion between fibers can be obtained, for example, by setting the heat treatment temperature to −50° C. to +10° C. of the melting point.

In addition, the projecting regions 15 shown in FIG. 16B have a communicating hole 155 on a side wall thereof. More specifically, the communicating hole 155 is a region where a distance between fibers constituting the side wall of the projecting region 15 is significantly large, and a region which looks like a break in a portion of the side wall.

For example, in a case where the composite sheet is disposed as a second sheet such that the projecting regions 15 face an absorbent core (not shown), menstrual blood of high viscosity running into the projecting regions 15 can be transferred to the absorbent core, without sticking thereon, via the communicating holes.

To form the abovementioned communicating holes 155 in the projecting regions 15 shown in FIG. 16B, for example, a draw ratio in a projecting portion forming step can be set higher than elasticity of a fiber aggregate.

As shown in FIG. 16C, a slit-like hole 156 is formed between the adjacent projecting regions 15. For example, in a case where the composite sheet is disposed as a second sheet such that the projecting regions 15 face an absorbent core (not shown), menstrual blood of high viscosity is transferred to the absorbent core via the slit-like holes and menstrual blood of low viscosity is transferred to the absorbent core via the projecting regions 15.

To form the slit-like holes 156 shown in FIG. 16C, for example, embossing processing is performed on a fiber aggregate having slits between regions in which the projecting regions 15 are formed, by way of the embossing roller device as shown in FIG. 23. This forms the holes 156 by widening the slits, while forming the projecting regions 15 as shown in FIG. 16A.

The projecting regions 15 shown in FIG. 16D have a communicating hole 155 formed in an apex thereof. For example, in a case where the composite sheet is disposed as a second sheet such that the projecting regions 15 face an absorbent core (not shown), menstrual blood of high viscosity running into the projecting regions 15 can be transferred to the absorbent core via the communicating holes, without plugging thereof.

The projecting regions 15 shown in FIG. 16D can be appropriately formed, for example, by way of the embossing roller device 900 in which the projections 921 that are formed on a surface of the second roller member 920, shown in FIG. 23, are pin-shaped and sharp.

3. Absorbent Article

As described above, the various composite sheets 10 according to the present invention can be used as the top sheet 2 or the second sheet 5 of the absorbent article 1. Supplement to the abovementioned modes and other modes are described in detail hereinafter.

3.1. Top Sheet

The composite sheets according to the abovementioned embodiments can be used as the top sheet of the absorbent article 1. For example, as shown in FIG. 17, the composite sheet 10 can be disposed such that a side on which the projecting regions 15 are formed faces a top side of the absorbent article 1, and the fiber aggregate 13 faces the absorbent core 4.

In this way, by contacting the tips of the projecting regions 15 with skin, it is possible for menstrual blood that runs along the skin to be caught by the tips of the projecting regions 15 and transferred to a side to the absorbent core 4. In addition, even if a large quantity of menstrual blood is discharged and surges into the projecting regions 15, the film sheet having the openings 110 can easily transfer the menstrual blood to the side to the absorbent core 4. In addition, since the absorbent article 1 contacts a skin surface in the plurality of projecting regions 15, an area of contact with the skin can be reduced, thereby lowering a negative impact on the skin, and backset of liquid under external pressure can be suppressed. This can prevent a sticky sensation imparted by the absorbent article 1.

In addition, as shown in FIG. 18, the composite sheet 10 can be disposed such that the projecting regions 15 face the absorbent core 4, and the fiber aggregate 13 faces the top side of the absorbent article 1. In such a case, liquid such as menstrual blood discharged onto the fiber aggregate 13 is transferred to the absorbent core 4 by the projecting regions 15. This can further provide a concealing effect, since the film sheet 11 suppresses backset of menstrual blood that is widely diffused by capillary force of the absorbent core 4. Disposing the composite sheet 10 as shown in FIG. 18 is preferable since the fiber aggregate 13 is exposed to a skin contacting side. Particularly, in a case where the film sheet 11 in the composite sheet 10 is deformed toward a projecting side of the projecting region 15, the skin contacting side is preferably a side on which the fiber aggregate 13 is disposed.

3.2. Second Sheet

A description is provided regarding a case where the composite sheets according to the abovementioned embodiments are used as the second sheet 5 of the absorbent article 1, with reference to FIGS. 19 to 22. The composite sheet 10 can be disposed so as to cover one entire side of the absorbent core 4, as shown in FIG. 19. In FIG. 19, although the composite sheet 10 is disposed such that the projecting regions 15 face the absorbent core 4 and the fiber aggregate 13 faces the top sheet 2, the composite sheet can also be disposed such that the projecting regions 15 face the top sheet 2 and the fiber aggregate 13 faces the absorbent core 4. The same applies to the composite sheet 10 shown in FIGS. 20 to 22 described later.

Here, in order to smoothly transfer liquid such as menstrual blood discharged on a surface of the top sheet 2, the composite sheet 10 is preferably disposed such that the projecting regions 15 face the absorbent core 4 and the fiber aggregate 13 faces the top sheet 2. In other words, the composite sheet 10 is preferably disposed such that the fiber aggregate 13 in the composite sheet 10 is in contact with the top sheet 2.

In addition, as shown in FIG. 20, the composite sheet 10 can be disposed on both sides in the width direction of the absorbent article 1. The composite sheet 10 can suppress side leakage even in a case where liquid such as menstrual blood runs in the width direction of the absorbent article 1, by drawing the liquid in. As described above, the composite sheet 10 can be disposed in both side portions in the width direction of the absorbent article 1, as a second sheet. In such a case, the composite sheet 10 can be disposed so as to direct the projecting regions 15 either to the top sheet or to the absorbent core 4. In addition, as described above, in order to smoothly transfer liquid such as menstrual blood discharged on a surface of the top sheet 2, the composite sheet 10 is preferably disposed such that the projecting regions 15 face the absorbent core 4 and the fiber aggregate 13 faces the top sheet 2. In other words, the composite sheet 10 is preferably disposed such that the fiber aggregate 13 in the composite sheet 10 is in contact with the top sheet 2.

In a case where the composite sheet 10 is used as the second sheet 5 of the absorbent article 1, backset of liquid that is once absorbed by the absorbent core 4 can be suppressed. For example, the film sheet 11 (for example, the U-shaped groove 113) suppresses backset of liquid to the fiber aggregate 13. Furthermore, liquid such as menstrual blood is dispersed on the film sheet 11 (for example, the U-shaped groove 113) in the line direction. This can suppress backset of liquid such as menstrual blood from the absorbent core 4. In a case where the composite sheet 10 according to the present embodiment is used as the second sheet 5, for example, an absorbent article 1 of superior concealing property for menstrual blood and superior backset suppressing ability can be obtained.

In addition, as shown in FIG. 21, another second sheet 6 can be further provided between the composite sheet 10 provided as the second sheet 5, which is disposed on both sides in the width direction of the absorbent article 1. In other words, the absorbent article 1 shown in FIG. 20 has another second sheet 6 disposed between the composite sheets 10 that are disposed on both sides in the width direction of the absorbent article 1.

Thus, the absorbent article 1 shown in FIG. 21 is in a preferable mode, having a concealing property and backset suppressing property in a central region thereof in the width direction, in addition to a side leakage suppressing ability, a concealing property, and a backset suppressing property as in the absorbent article 1 shown in FIG. 20.

In addition, the absorbent article 1 shown in FIG. 22 is the absorbent article 1 shown in FIG. 21 further including a second sheet 7, which is another fiber aggregate. Furthermore, in the absorbent article 1 shown in FIG. 22, a density of the fiber aggregate 13 in the composite sheet 10, which is disposed on both sides in the width direction of the absorbent article 1, is high.

The fiber aggregate 13 in the composite sheet 10 has a higher density than, for example, the fiber aggregate as the second sheet 6 disposed in the center. In other words, for example, a thickness "a" (bulkiness) of the fiber aggregate, which is the second sheet 6, is greater than a thickness "b" (bulkiness) of the fiber aggregate 13 in the composite sheet 10.

With such a configuration, in a case where menstrual blood flows to both sides of the top sheet 2, a coarse-dense gradient provided by the high density fiber aggregate 13 in the composite sheet 10 can appropriately draw menstrual blood on the top sheet 2 to the absorbent core 4.

In addition, in a state that liquid such as menstrual blood that is absorbed by the absorbent core 4 is diffused to both sides in the width direction, even if external pressure is applied to the absorbent article 1, the other second sheet 7 can suppress transfer of the liquid such as menstrual blood to the top sheet 2.

It should be noted that, although a case is described in which the film sheet 11 is completely split and the projecting regions 15 are completely exposed (in other words, the apexes of the projecting regions are composed only of fiber aggregate) in the above configuration, the film sheet 11 is not required to be completely split, provided that transfer property for liquid such as menstrual blood is not affected. For example, the film sheet 11 can be present on the apexes of the projecting regions. In such a case, a thickness of the film sheet 11 present on the apexes of the projecting regions 15 is 3 to 20 µm, and preferably 5 to 10 µm (the same applies to a case where microopenings with valves are provided in advance).

4. Evaluation Method

A residual liquid ratio (liquid drawing ability, spot property) and a backset suppressing ability (rewet suppressing ability) can be evaluated using artificial menstrual blood.

As measurement apparatuses, for example, (1) an autoburette (type 725, manufactured by Metrohm AG), (2) a perforated acrylic plate (200 mm in length, 100 mm in width and 130 g in weight, with a hole of 40 mm×10 mm in a center thereof), (3) scales, (6) a ruler, (5) artificial menstrual blood, (6) a chronograph, and (7) filter paper are used.

An evaluation sample is prepared as follows. First, a sheet is cut to a size of 100 mm in length and 60 mm in width (arbitrary), and the basis weight and thickness thereof are measured. Next, an absorbent core is obtained by wrapping an NB pulp absorbent core with a tissue of 15 gsm and cut to a size of 100 mm×60 mm. Then, the absorbent core is pressed flat to adjust the density and the like thereof (basis weight: 500 g/m$^2$, density: 0.09 g/cm$^3$).

The residual liquid ratio is evaluated according to the following steps.

1. Placing the test piece (sheet) on the absorbent core.
2. Placing the acrylic plate thereon, with the hole centered.
3. Setting a nozzle of the autoburette at 10 mm above the acrylic plate.
4. Dropping 1 ml of the artificial menstrual blood at a rate of 7 ml/min.
5. Removing the acrylic plate 1 minute after starting dropping.
6. Measuring the mass of the sheet and calculating the residual liquid ratio.

The backset suppressing ability (rewet suppressing ability) is evaluated according to the following steps.

1. After measuring the mass, putting the top sheet back, and placing the filter paper, the acrylic plate, and a weight thereon, in this order.
2. Leaving for a minute with the weight thereon.
3. Measuring the mass of the filter paper and calculating the backset ratio.

The invention claimed is:

1. A composite sheet, comprising:
    a film sheet having a plurality of openings and/or a plurality of slits; and
    a fiber aggregate layered on a first side of the film sheet, wherein
    the fiber aggregate includes a plurality of projecting regions that project to a second side of the film sheet opposite to the first side, through the plurality of openings and/or the plurality of slits, each of the projecting regions including a base portion,
    the film sheet includes a groove disposed between a pair of adjacent projecting regions among the plurality of projecting regions and having
        a bottom
        two branches both extending from the bottom in a projecting direction of the projecting regions and covering at least a portion of the base portion of one of the adjacent projecting regions, and the projecting regions are disposed in a staggered manner.

2. The composite sheet according to claim 1, wherein the groove extends in a straight line or in a curved line in a predetermined direction.

3. The composite sheet according to claim 2, wherein
    the film sheet comprises two grooves extending side by side in the predetermined direction and between said two adjacent projecting regions, and
    each of the grooves extends in the curved line in the predetermined direction.

4. The composite sheet according to claim 1, further comprising another fiber aggregate including cellulosic fiber and disposed on said fiber aggregate, said film sheet being arranged between said fiber aggregates.

5. An absorbent article, comprising:
a top sheet that is at least partially liquid permeable, and includes the composite sheet according to claim 1 in at least a portion thereof;
a back sheet that is liquid impermeable; and
an absorbent core, which is liquid retentive, disposed between the top sheet and the back sheet,
wherein the plurality of projecting regions faces toward the absorbent core.

6. An absorbent article of an elongated shape, comprising:
a top sheet that is at least partially liquid permeable;
a back sheet that is liquid impermeable;
an absorbent core, which is liquid retentive, disposed between the top sheet and the back sheet; and
a second sheet that is at least partially liquid permeable and disposed between the top sheet and the absorbent core, and includes the composite sheet according to claim 1 in at least a portion thereof,
wherein
the plurality of projecting regions faces toward the absorbent core.

7. The absorbent article according to claim 6, wherein
the fiber aggregate of the composite sheet has a first portion in direct contact with the groove and a second portion free of direct contact with the groove, and
the first portion of the fiber aggregate is in direct contact with a lower side of the top sheet.

8. The composite sheet according to claim 1, wherein each of the projecting regions includes a communicating hole on an apex or on a side face thereof.

9. The composite sheet according to claim 1, wherein a distance between said two adjacent projecting regions in a first direction is from −5 to 10 mm, and
a negative value of the distance indicates that the adjacent projecting regions overlap each other without a gap when viewed from a second direction orthogonal to the first direction.

10. The composite sheet according to claim 1, wherein the groove continuously extends in a predetermined direction and along the plurality of projecting regions arranged in the predetermined direction.

11. The composite sheet according to claim 1, wherein two grooves are arranged between said pair of adjacent projecting regions.

12. The composite sheet according to claim 11, wherein said two grooves between said two adjacent projecting regions are separated from each other and are not formed in one piece.

13. A method of manufacturing a composite sheet, said method comprising:
disposing a substantially fiber aggregate on a first side of a film sheet to define a composite sheet; and
pushing the composite sheet by a predetermined projecting region forming device from the first side of the film sheet toward a second side of the film sheet, said second side being opposite to the first side, to form a plurality of projecting regions projecting from the second side of the film sheet
wherein the predetermined projecting region forming device includes
a first member having a plurality of openings that are disposed in a staggered manner; and
a second member having a plurality of projections that correspond to the plurality of openings and are disposed in the staggered manner to form the projecting regions arranged in the staggered manner.

14. The method according to claim 13, wherein,
the first member has a flat surface or a curved surface with the plurality of openings, and
the second member has a flat surface or a curved surface with the plurality of projections
the flat surface or the curved surface of the second member faces toward the flat surface or the curved surface of the first member, and
the film sheet faces toward the first member and the fiber aggregate faces toward the second member,
the composite sheet is tucked between the first member and the second member such that at least one of the plurality of projections of the second member engages with at least one of the plurality of openings of the first member, so as to form the plurality of projecting regions.

15. The method according to claim 14, wherein a draw ratio caused by the projections is higher than an elasticity of the film sheet in a direction between the first side and the second side.

16. The method according to claim 13, wherein the film sheet is a low-elasticity film sheet.

17. A method of manufacturing an absorbent article, comprising
providing a sheet which has a portion that includes the composite sheet manufactured according to the method of claim 13, and
providing an absorbent core below the composite sheet in a thickness direction thereof, wherein the film sheet of the composite sheet faces toward the absorbent core.

* * * * *